(12) United States Patent
Wilson et al.

(10) Patent No.: US 12,062,178 B2
(45) Date of Patent: Aug. 13, 2024

(54) AUTOMATED SEGMENTATION AND GUIDED CORRECTION OF ENDOTHELIAL CELL IMAGES

(71) Applicant: Case Western Reserve University, Cleveland, OH (US)

(72) Inventors: David L. Wilson, Cleveland Heights, OH (US); Naomi Joseph, Cleveland, OH (US); Jonathan H. Lass, Cleveland, OH (US); Beth Ann Benetz, Cleveland, OH (US); Harry J. Menegay, Cleveland, OH (US); Elizabeth Fitzpatrick, Nashville, TN (US)

(73) Assignee: Case Western Reserve University, Cleveland, OH (US)

( * ) Notice: Subject to any disclaimer, the term of this patent is extended or adjusted under 35 U.S.C. 154(b) by 547 days.

(21) Appl. No.: 17/141,564

(22) Filed: Jan. 5, 2021

(65) Prior Publication Data
US 2021/0278655 A1 Sep. 9, 2021

Related U.S. Application Data

(60) Provisional application No. 62/985,481, filed on Mar. 5, 2020.

(51) Int. Cl.
*G06T 7/11* (2017.01)
*C12N 5/079* (2010.01)
(Continued)

(52) U.S. Cl.
CPC ............ *G06T 7/11* (2017.01); *C12N 5/0621* (2013.01); *G02B 21/367* (2013.01); *G06T 7/10* (2017.01);
(Continued)

(58) Field of Classification Search
CPC .................... G06T 7/10–194; G06V 10/44
See application file for complete search history.

(56) References Cited

U.S. PATENT DOCUMENTS

2014/0198979 A1* 7/2014 Hamarneh .............. G06T 7/174
382/154
2020/0234433 A1* 7/2020 Tanaka ............... G01N 33/5067

OTHER PUBLICATIONS

Daniel, Moritz C., et al. "Automated segmentation of the corneal endothelium in a large set of 'real-world' specular microscopy images using the U-Net architecture." Scientific reports 9.1 (2019): 4752. (Year: 2019).*

(Continued)

*Primary Examiner* — Vincent Rudolph
*Assistant Examiner* — Raphael Schwartz
(74) *Attorney, Agent, or Firm* — Eschweiler & Potashnik, LLC

(57) ABSTRACT

Embodiments discussed herein facilitate automated and/or semi-automated segmentation of endothelial cells via a trained deep learning model. One example embodiment is a method, comprising: accessing an optical microscopy image comprising a set of corneal endothelial cells of a patient of a keratoplasty; pre-processing the optical microscopy image to generate a pre-processed optical microscopy image via correcting for at least one of shading or illumination artifacts in the optical microscopy image; segmenting, based at least in part on a trained deep learning (DL) model, a plurality of corneal endothelial cells of the set of corneal endothelial cells in the pre-processed optical microscopy image; and displaying, via a graphical user interface (GUI), at least the segmented plurality of corneal endothelial cells.

24 Claims, 29 Drawing Sheets

(51) Int. Cl.
  G02B 21/36    (2006.01)
  G06T 7/10     (2017.01)
  G06V 10/44    (2022.01)
  G06V 10/764   (2022.01)
  G06V 10/82    (2022.01)
  G06V 20/69    (2022.01)
(52) U.S. Cl.
  CPC ............ G06V 10/44 (2022.01); G06V 10/764 (2022.01); G06V 10/82 (2022.01); G06V 20/695 (2022.01); *G06T 2207/30024* (2013.01)

(56) References Cited

OTHER PUBLICATIONS

Nadachi, Ryoichi, and Kazuo Nunokawa. "Automated corneal endothelial cell analysis." [1992] Proceedings Fifth Annual IEEE Symposium on Computer-Based Medical Systems. IEEE, 1992. (Year: 1992).*

Fabijańska, Anna. "Segmentation of corneal endothelium images using a U-Net-based convolutional neural network." Artificial intelligence in medicine 88 (2018): 1-13. (Year: 2018).*

* cited by examiner

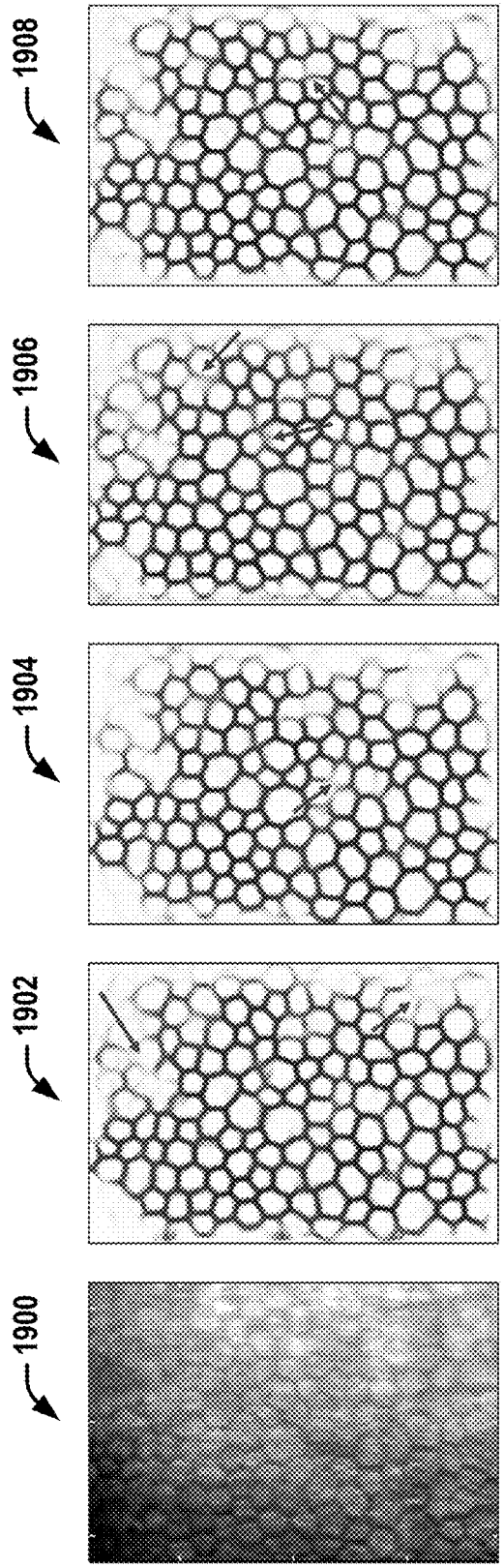
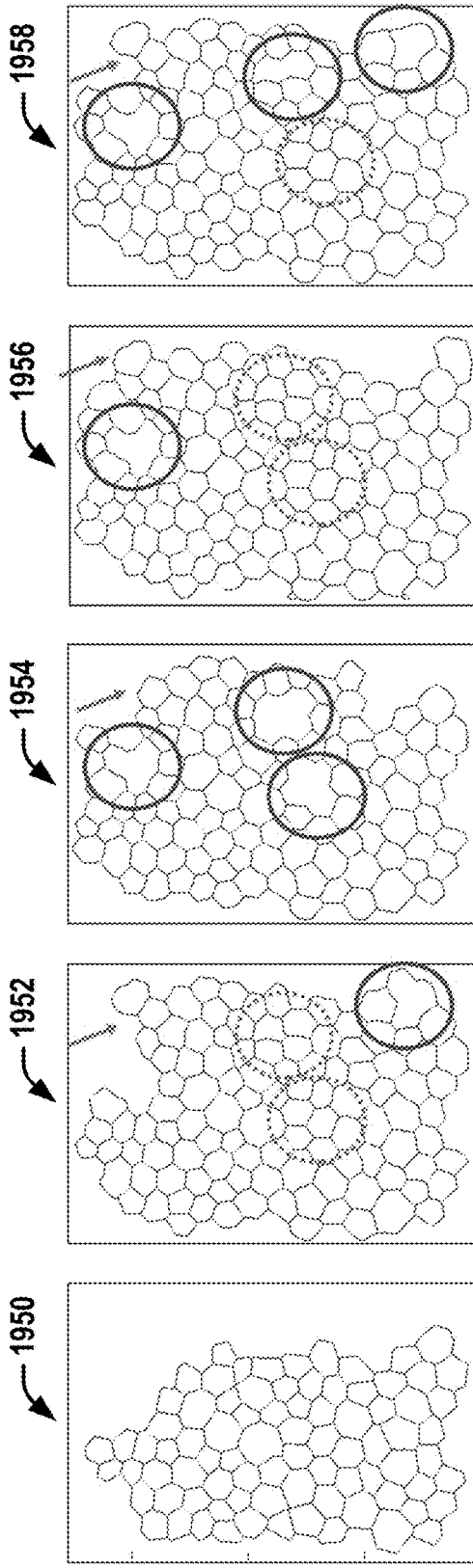
FIG. 19A
FIG. 19B

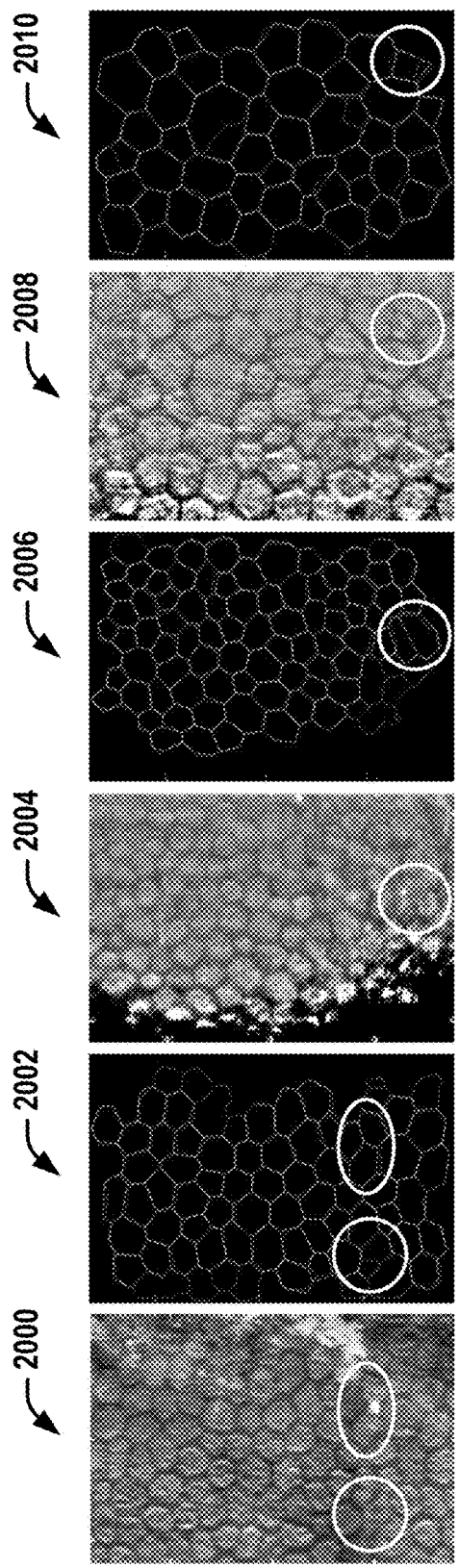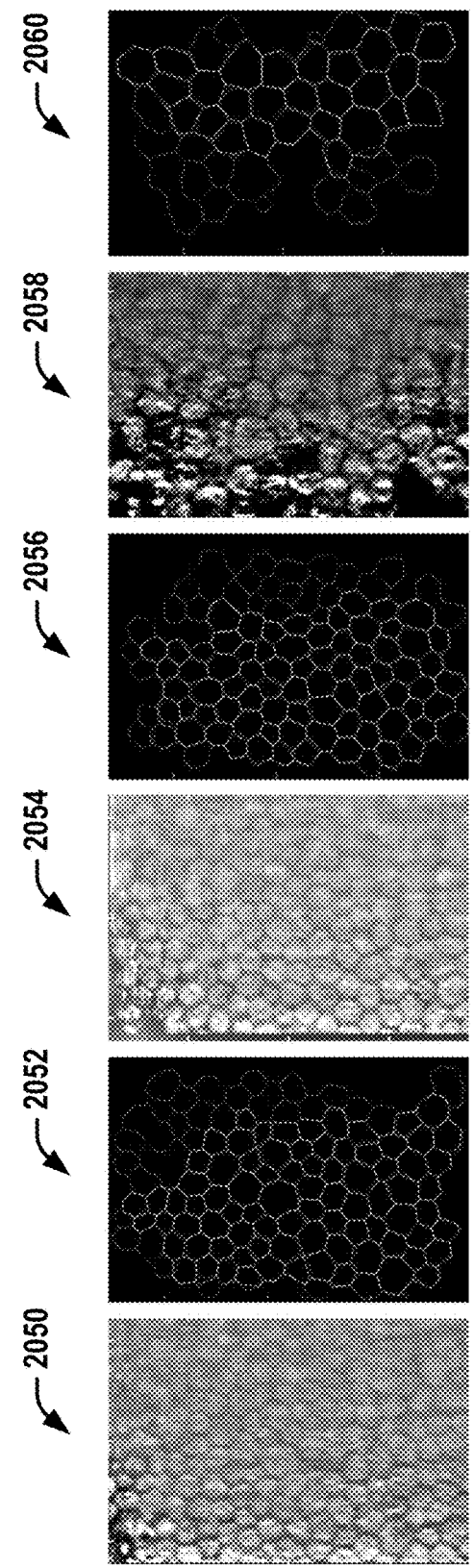
FIG. 20A
FIG. 20B

AUTOMATED SEGMENTATION AND GUIDED CORRECTION OF ENDOTHELIAL CELL IMAGES

CROSS REFERENCE TO RELATED APPLICATIONS

This application claims the benefit of U.S. Provisional Patent Application No. 62/985,481 filed Mar. 5, 2020, entitled "AUTOMATED SEGMENTATION AND GUIDED CORRECTION OF ENDOTHELIAL CELL IMAGES", the contents of which are herein incorporated by reference in their entirety.

FEDERAL FUNDING NOTICE

This invention was made with government support under the grant(s) EY029498 awarded by the National Institutes of Health. The government has certain rights in the invention.

BACKGROUND

The Eye Bank Association of America (EBAA) reported 48,366, corneal keratoplasties performed in the US in 2017, with 28,993 endothelial keratoplasty (EK) and 18,346 penetrating keratoplasty (PK) procedures. The regraft rate for 2016 was 8.8% for EK and 11.8% for PK, where graft failure involves regrafting for any reason or a cornea which remains cloudy without clearing for at least 90 days of observation.

BRIEF DESCRIPTION OF THE DRAWINGS

The accompanying drawings, which are incorporated in and constitute a part of the specification, illustrate various example operations, apparatus, methods, and other example embodiments of various aspects discussed herein. It will be appreciated that the illustrated element boundaries (e.g., boxes, groups of boxes, or other shapes) in the figures represent one example of the boundaries. One of ordinary skill in the art will appreciate that, in some examples, one element can be designed as multiple elements or that multiple elements can be designed as one element. In some examples, an element shown as an internal component of another element may be implemented as an external component and vice versa. Furthermore, elements may not be drawn to scale.

FIG. 19A illustrates images of deep learning probability maps of an example test image following four types of pre-processing, in connection with various aspects discussed herein.

FIG. 19B illustrates images showing the final segmentation results of the EC image of FIG. 20 with the four pre-processing methods discussed above, according to various aspects discussed herein.

FIG. 20A illustrates three example EC images and corresponding segmentation highlighting cells with differences between manual and automatic segmentations, in connection with various aspects discussed herein.

FIG. 20B illustrates three examples of EC images showing the automatic segmentation method identifying and segmenting cells outside of the sample area of the ground truth annotations, in connection with various aspects discussed herein.

DETAILED DESCRIPTION

Figure 1:
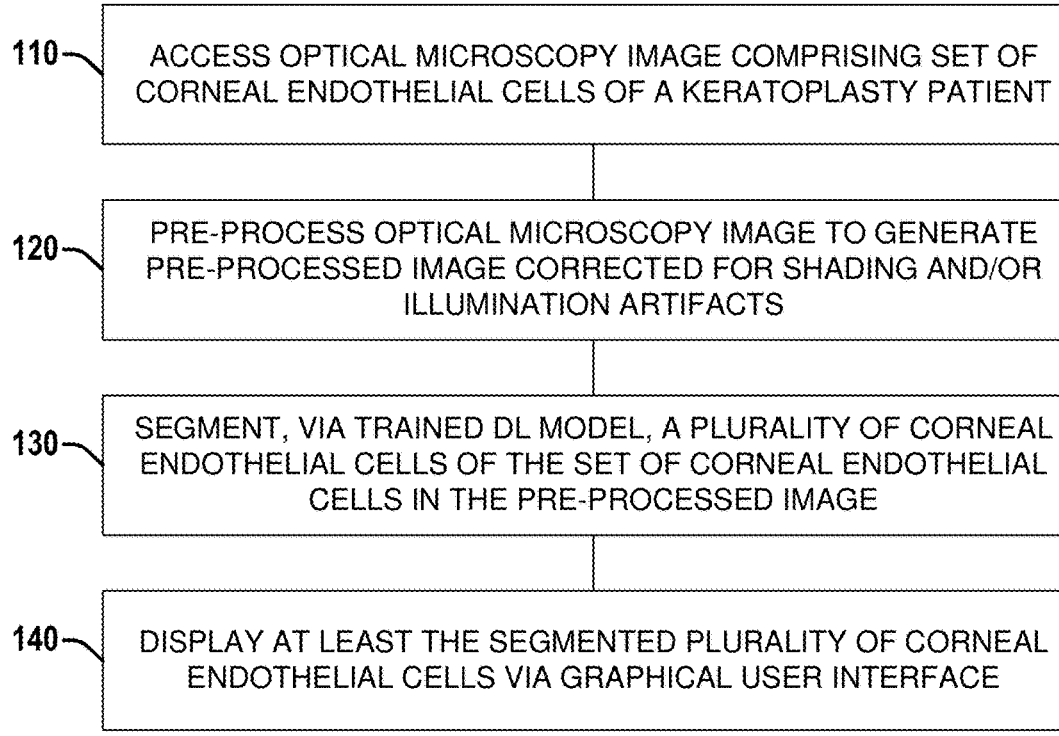
FIG. 1 illustrates a flow diagram of an example method/set of operations that can be performed by one or more processors to segment corneal endothelial cells in an automatic and/or semi-automatic manner via a trained deep learning model, according to various aspects discussed herein.

In light of the risks of graft failure via rejection or otherwise, successful predictive image analytics of potential failure can be advantageous. Via increased surveillance, patients can be identified for tailoring topical corticosteroid usage associated with some glaucoma risk, and counseling can be intensified to improve patient compliance. Compliance with medication is an issue with corneal grafts, and it is likely that interventions could improve results in a manner similar to the well-studied effect in glaucoma. Saving the initial graft is quite important, as there is a significant increase in rejection rate in a second graft, with mechanisms identified in mouse studies. By identifying possible rejection at a subclinical level, this could potentially reduce graft rejection failures significantly. Various embodiments can facilitate the identification of potential rejection and/or graft failure, which can reduce health care costs, patient discomfort, patient angst, and vision loss.

Evidence suggests that corneal EC images could predict graft rejection and failure. The corneal endothelium plays a critical role in maintaining stromal clarity. A sufficient number of endothelial cells, serving as Na+/K+-ATPase pump sites, are required to prevent corneal swelling which impairs vision and can ultimately lead to graft failure. The normal endothelial cell layer has a regular hexagonal structure (nature's preferred cellular arrangement, as described below). The literature suggests that changes in morphometric measures, including coefficient of variation (CV) of cell area (polymegathism) and the percentage of hexagonal cells or hexagonality (HEX), reflecting variation in cell shape (pleomorphism), may be more sensitive than endothelial cell density (ECD) in assessing endothelial health and dysfunction. Research performed in connection with various embodiments based on the National Eye Institute-sponsored Specular Microscopy Ancillary Study (SMAS) images found that 6-month HEX results were suggestive of an association with subsequent late graft failure, whereas CV was not predictive of graft failure. Consultants, Drs. Baydoun and Melles of the Netherlands Institute for Innovative Ocular Surgery (NIIOS), created a scoring system predictive of corneal rejection after Descemet Membrane Endothelial Keratoplasty (DMEK) surgery. In addition to CV and HEX, they described visual subjective scoring related to the cell morphology pattern and distribution, cellular reflectivity, presence/size of cell nuclei and appearance of cellular activation. Scoring metrics were determined by comparing rejection and non-rejection image groups, a process systematized in connection with various embodiments and the example use cases discussed below.

Various embodiments discussed herein can comprise and/or employ techniques that can facilitate segmenting corneal endothelial cells and/or training a deep learning model to perform such segmentation. Various embodiments can be applied to corneal endothelial cells images acquired with various types of specular and confocal microscopes.

Some portions of the detailed descriptions that follow are presented in terms of algorithms and symbolic representations of operations on data bits within a memory. These algorithmic descriptions and representations are used by those skilled in the art to convey the substance of their work to others. An algorithm, here and generally, is conceived to be a sequence of operations that produce a result. The operations may include physical manipulations of physical quantities. Usually, though not necessarily, the physical quantities take the form of electrical or magnetic signals capable of being stored, transferred, combined, compared, and otherwise manipulated in a logic or circuit, and so on. The physical manipulations create a concrete, tangible, useful, real-world result.

It has proven convenient at times, principally for reasons of common usage, to refer to these signals as bits, values, elements, symbols, characters, terms, numbers, and so on. It should be borne in mind, however, that these and similar terms are to be associated with the appropriate physical quantities and are merely convenient labels applied to these quantities. Unless specifically stated otherwise, it is appreciated that throughout the description, terms including processing, computing, calculating, determining, and so on, refer to actions and processes of a computer system, logic, circuit, processor, or similar electronic device that manipulates and transforms data represented as physical (electronic) quantities.

Example methods and operations may be better appreciated with reference to flow diagrams. While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, less than all the illustrated blocks may be required to implement an example methodology. Blocks may be combined or separated into multiple components. Furthermore, additional and/or alternative methodologies can employ additional, not illustrated blocks.

Referring to FIG. 1, illustrated is a flow diagram of an example method/set of operations 100 that can be performed by one or more processors to segment corneal endothelial cells in an automatic and/or semi-automatic manner via a trained deep learning model, according to various aspects discussed herein.

The set of operations 100 can comprise, at 110, accessing an optical microscopy image comprising a set of corneal endothelial cells of a patient of a keratoplasty. In various embodiments and in the example use cases discussed below, the image can be obtained via a system and/or apparatus implementing the set of operations 100, or can be obtained from a separate medical imaging system. Additionally, the training set of images can be accessed contemporaneously with or at any point prior to performing the set of operations 100.

The set of operations 100 can further comprise, at 120, pre-processing the optical microscopy image to generate a pre-processed optical microscopy image via correcting for at least one of shading or illumination artifacts in the optical microscopy image;

The set of operations 100 can further comprise, at 130, segmenting, based at least in part on a trained deep learning (DL) model, a plurality of corneal endothelial cells of the set of corneal endothelial cells in the pre-processed optical microscopy image.

The set of operations 100 can further comprise, at 140, displaying, via a graphical user interface (GUI), at least the segmented plurality of corneal endothelial cells.

Additionally or alternatively, set of operations 100 can comprise one or more other actions discussed herein in connection with employing a trained DL model to automatically and/or semi-automatically segment endothelial cells.

Figure 2:
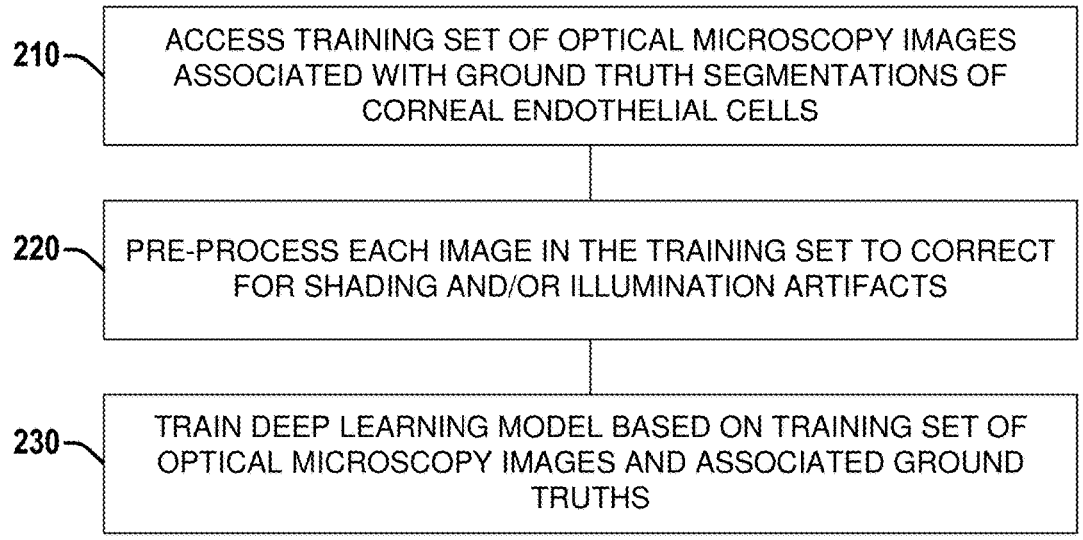
FIG. 2 illustrates a flow diagram of an example method/set of operations that can be performed by one or more processors to train a model via deep learning to segment endothelial cells, according to various aspects discussed herein.

Referring to FIG. 2, illustrated is a flow diagram of an example method/set of operations 200 that can be performed by one or more processors to train a model via deep learning to segment endothelial cells, according to various aspects discussed herein.

The set of operations 200 can comprise, at 210, accessing a training set of optical microscopy images of corneal endothelial cells, wherein each image can be associated with a ground truth segmentation of its endothelial cells. In various embodiments and in the example use cases discussed below, the images can be obtained via a system and/or apparatus implementing the set of operations 200, or can be obtained from a separate medical imaging system. Additionally, the images can be accessed contemporaneously with or at any point prior to performing the set of operations 200.

The set of operations 200 can further comprise, at 220, pre-processing each optical microscopy image of the training set to correct for at least one of shading or illumination artifacts.

The set of operations 200 can further comprise, at 230, training a model via deep learning based on the training set of images and the associated ground truth segmentations of the endothelial cells of each image of the training set.

Additionally or alternatively, set of operations 200 can comprise one or more other actions discussed herein in connection with training a model via deep learning to segment endothelial cells.

Figure 3:
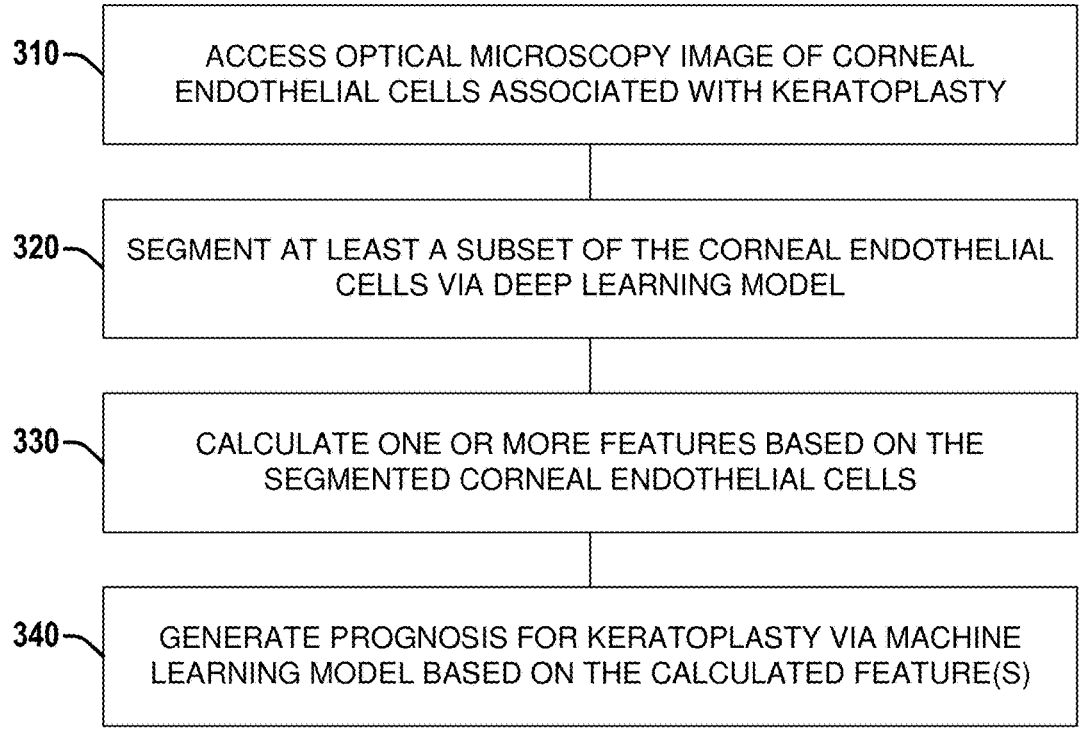
FIG. 3 illustrates a flow diagram of an example method/set of operations that can be performed by one or more processors to determine a prognosis for a keratoplasty based on features calculated from segmented corneal endothelial cells, according to various aspects discussed herein.

Referring to FIG. 3, illustrated is a flow diagram of an example method/set of operations 300 that can be performed by one or more processors to determine a prognosis for a keratoplasty based on features calculated from segmented corneal endothelial cells, according to various aspects discussed herein. Processor(s) can include any combination of general-purpose processors and dedicated processors (e.g., graphics processors, application processors, etc.). The one or more processors can be coupled with and/or can include memory or storage and can be configured to execute instructions stored in the memory or storage to enable various apparatus, applications, or operating systems to perform the operations. The memory or storage devices may include main memory, disk storage, or any suitable combination thereof. The memory or storage devices can comprise—but is not limited to—any type of volatile or non-volatile memory such as dynamic random access memory (DRAM), static random-access memory (SRAM), erasable programmable read-only memory (EPROM), electrically erasable programmable read-only memory (EEPROM), Flash memory, or solid-state storage.

The set of operations 300 can comprise, at 310, accessing an optical microscopy image of corneal endothelial cells of a keratoplasty patient. In various embodiments and in the example use cases discussed below, the image can be obtained via a system and/or apparatus implementing the set of operations 300, or can be obtained from a separate medical imaging system (e.g., specular or confocal microscope, etc.). Additionally, the image can be accessed contemporaneously with or at any point prior to performing the set of operations 300.

The set of operations 300 can further comprise, at 320, segmenting at least a subset of the corneal endothelial cells of the image via a deep learning model, according to techniques discussed herein. For example, segmenting the corneal endothelial cells can comprise pre-processing the image, generating an output probability image via the deep learning model, generating a binarized output via thresholding, and thinning cell boundaries, each of which can be according to techniques discussed herein.

The set of operations 300 can further comprise, at 330, calculating one or more features associated with the segmented endothelial cells. The one or more features can comprise existing measures (e.g., endothelial cell density (ECD), coefficient of variation (CV) of cell area, hexagonality (HEX), etc.), one or more graph features (e.g., local or global graph features of any of the types discussed herein, etc.), or one or more other features discussed herein, including novel features introduced herein.

The set of operations 300 can further comprise, at 340, generating a prognosis for the keratoplasty (e.g., of rejection, failure or non-failure; of one of no adverse outcome, non-rejection failure, or rejection; etc.) based on the one or more calculated features via a trained model (e.g., a machine learning (ML) model such as a Linear Discriminant Analysis (LDA) classifier, a Quadratic Discriminant Analysis (QDA) classifier, a Support Vector Machine (SVM) classifier, or a Random Forest (RF) classifier, etc., another type of model, etc.).

Additionally or alternatively, set of operations 300 can comprise one or more other actions discussed herein in connection with determining a prognosis for keratoplasty based at least in part on features calculated from segmented endothelial cells.

Additional aspects and embodiments are discussed below in connection with the following example use cases.

Example Use Case 1: Assessment of Endothelial Cells and Corneas at Risk from Ophthalmological Images The following discussion provides example embodiments in connection with a first example use case involving analyzing the images of cornea endothelial cells and determination of the degradation of these important cells maintaining corneal clarity.

1. Overview

Review of CWRU's NIH-Funded Cornea Donor Study (CDS) with the Attached Specular Microscopy Ancillary Study (SMAS) and the Cornea Preservation Time Study (CPTS).

The first example use case was developed based on enhanced understanding, obtained from the CDS, of many factors surrounding the success of penetrating keratoplasty (PK) for conditions with endothelial dysfunction, notably Fuchs dystrophy and pseudophakic/aphakic corneal edema. In the associated SMAS, endothelial cell loss (ECL) was assessed in a subset of participants to examine its relationship with donor age. A slight association between increasing donor age and greater post-PKP corneal endothelial cell loss by 5 years was found among eyes whose grafts were successful at 5 years. Endothelial Cell Density (ECD) at 6 months, 1 year and 5 years was strongly predictive with subsequent graft failure. The CPTS data provides important information related to ECL following Descemet stripping automated endothelial keratoplasty (DSAEK) at three years related to storage time as well as the impact of donor, recipient, surgical and post-surgical factors on graft success and EC health. Since the literature suggests that changes in morphometrics (coefficient of variation (CV) of cell area and percentage of hexagonal cells or hexagonality (HEX)) may be more sensitive than ECD in assessing endothelial health and dysfunction, this was examined in connection with the first example use case in a case-comparison group study from a subset of SMAS participants. It was found that 6-month HEX results suggested an association with subsequent graft failure, whereas CV was not predictive of graft failure. The first example use case examined image analytics, as a more sensitive predictor of graft failure.

Review of Image Processing Solutions.

Recent papers demonstrate approaches in computerized image analysis of EC images as obtained from specular microscopes and, less commonly, confocal microscopes. There is opportunity for improved software. High-quality images in publications lead to concern about performance in clinical practice. Some recent papers use uncommon confocal rather than specular microscopy. Several reports describe limited performance of commercial systems clinically, suggesting a need for improvement. Nearly the entire focus has been on ECD, CV, and HEX, suggesting an opportunity to uncover new, important morphological and cell disarray image attributes, such as those discussed herein. Moreover, no quantitative paper has investigated image attributes associated with keratoplasty rejection.

Opportunity with Machine Learning.

There are many success stories showing the ability of medical image analytics to predict clinical outcomes in cancer, Alzheimer's, and more. There has been particular success when applying image analytics to histology. In head-to-head comparisons, some studies show that image analytics can outperform physician experts, for example, at prediction of brain tumor recurrence, in a study from the Case Western Reserve University (CWRU) Center of Computational Imaging and Personalized Diagnostics (CCIPD). Given the linkage between EC images and cornea health, reports on EC quantitative biomarkers, and promise of machine learning, it is likely that image analytics will predict keratoplasty failures much better than current strategies.

Data.

The quality and quantity of aggregated data allowed for high quality machine learning solutions to be created in connection with the first example use case. The data sources included the following. SMAS (EY12728, EY012358) over a 10-year observation window includes 609 subjects with 105 failures with 8 imaging time points (6 mo, 1 Y, 2 Y, 3 Y, 4 Y, 5 Y, 7/8 Y, and 10 Y), each with 3 image repeats, giving 14,616 total images (2,520 failure images), minus drop out or deceased individuals. CPTS (EY020798) includes 1330 eyes at 5 time points (baseline, 6 months, 1, 2 and 3 years), each with 3 image repeats. Assuming a 10% failure rate, there are 15,960 total images (1,596 failure images). CNIIOS will consist of at least 50 failures and 100 matching no-failures, at about 6 time points with 3 repeats. This gives 2,700 total images (900 failure images). Altogether, the data comprises 31,476 total images with about 5,016 images from eyes with a graft failure. For the first example use case, focusing on the predictive value of 6 month images, there were an estimated 6,267 images with 864 images from eyes with eventual graft failure. These images are all well-curated, manually analyzed images.

Advantages.

As demonstrated by the first example use case, various embodiments can detect keratoplasties at risk of failing and/or rejection, leading to early interventions that would reduce failures and/or rejections. Saving the initial keratoplasty is quite important, as there is a greater rejection rate in a second keratoplasty. Embodiments can provide multiple advantages, including reduced health care costs, patient discomfort, patient angst, and vision loss. Various embodiments can employ techniques discussed herein using specular (and/or confocal) microscopic images and image analytics to predict corneas at risk. The first example use case and various embodiments also introduce novel concepts and approaches to keratoplasty rejection and failure prediction. Various embodiments can use powerful image analytics approaches to predict corneal grafts at risk. Computational features employed can comprise graph analytics approaches that improve upon current HEX measures by assessing disarray both between neighboring cells and cells in the more distant surrounding area. Other features can objectively evaluate attributes identified by the NIIOS group in their visual scoring system for predicting early rejection.

Motivation for Image Analytics Approach.

Normal EC images are comprised of compact, very regular hexagonal arrays of cells. In nature, the hexagonal structure is preferred to other ones that provide perfect coverage with thin membranes (only squares and triangles), because the hexagonal structure maximizes the area per cell while minimizing the number of cells required to provide coverage, and minimizes length of contact to create the "least interface energy". Hence, there is a substantive history of computing quantitative biomarkers (e.g., ECD and HEX) to assess cornea health. The first example use case studied graph analytics that capture the full expression of structural disarray in non-normal EC images. Previously, many have described other EC image attributes, e.g., intracellular dark circles corresponding to nuclei, intracellular bright punctate corresponding to pigment deposits, intracellular dark structures corresponding to vacuoles, and dark structures at cell intersections corresponding to invading white blood cells. Consultants Baydoun and Melles implicated visual attributes with keratoplasty rejection by visually comparing images from eyes with and without rejection. The first example use case computed a number of morphometric and intensity-based image features that capture the essence of these attributes and more. The features analyzed in the first example use case provide very rich inputs from images that would be very difficult for a person, but easy for a computer, to compare between sets of failure and no-failure images. Results obtained in connection with the first example use case show that these features can distinguish normal and abnormal EC images.

2. Techniques

The first example use case comprised several different techniques. To enable routine, objective evaluation of corneas at risk, processing can be either fully automated or highly automated. The techniques employed in the first example use case comprise: (1) Segmentation of endothelial cells; (2) Determination of classic EC metrics; (3) Determination of cellular features; and (4) Determination of corneas at risk. Each of these techniques is described in greater detail below.

Figure 4:
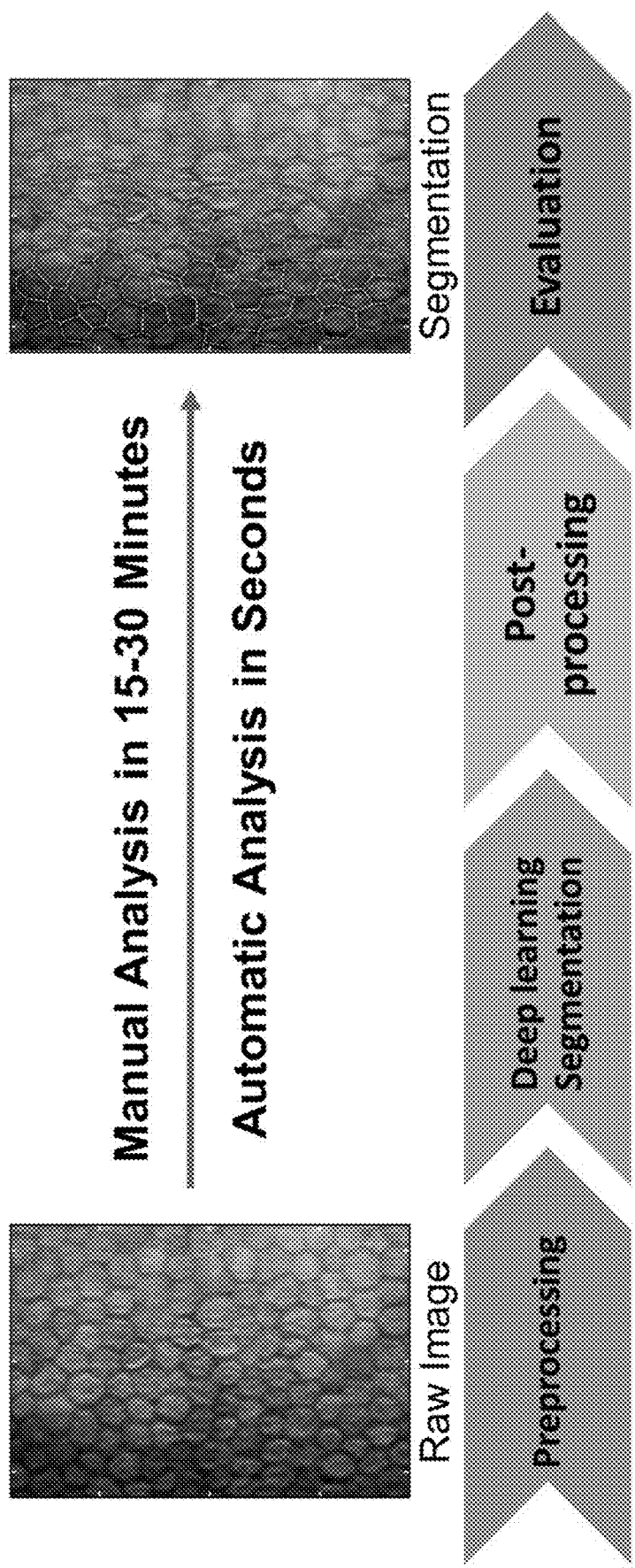
FIG. 4 illustrates a time comparison overview of the manual and automated techniques employed to segment an initial and raw endothelial cell image along with the flow diagram of the implemented automatic segmentation algorithm, in connection with various aspects discussed herein.

Referring to FIG. 4, illustrated is an overview of the techniques employed in the first example use case, along with an initial and endothelial cell segmented version of an example EC image, in connection with various aspects discussed herein. When segmenting EC images, a cell-border was defined for the first example use case as a collection of curve segments enclosing a bright cell. Manual segmentation of an image might take 15-30 minutes. Automatic analysis according to aspects discussed herein can reduce this time to seconds.

Figure 5:
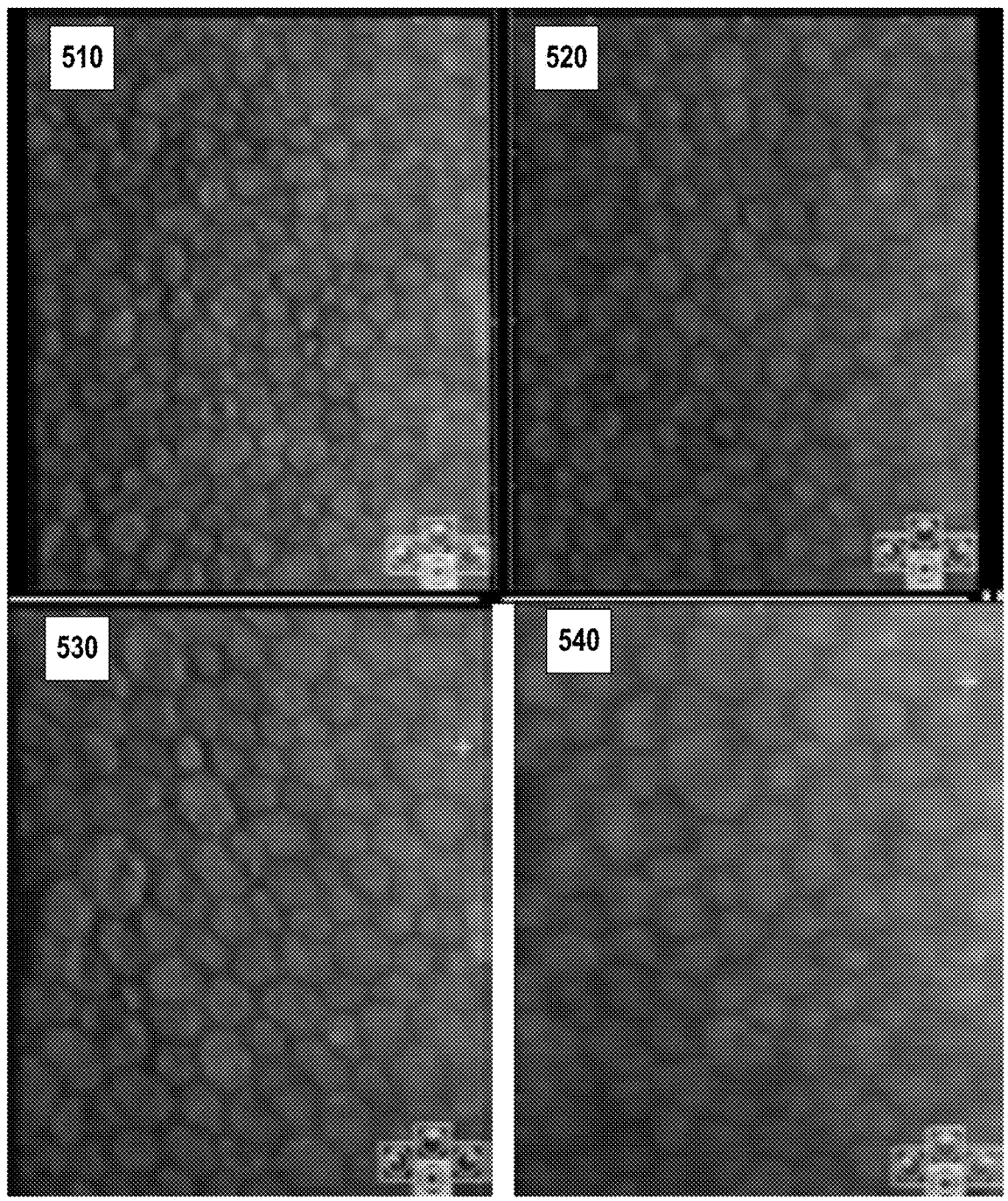
FIG. 5 illustrates serial specular microscope imaging following a penetrating keratoplasty (PK) procedure showing a continuing decrease in endothelial cell density, in connection with various aspects discussed herein.
Figure 6:
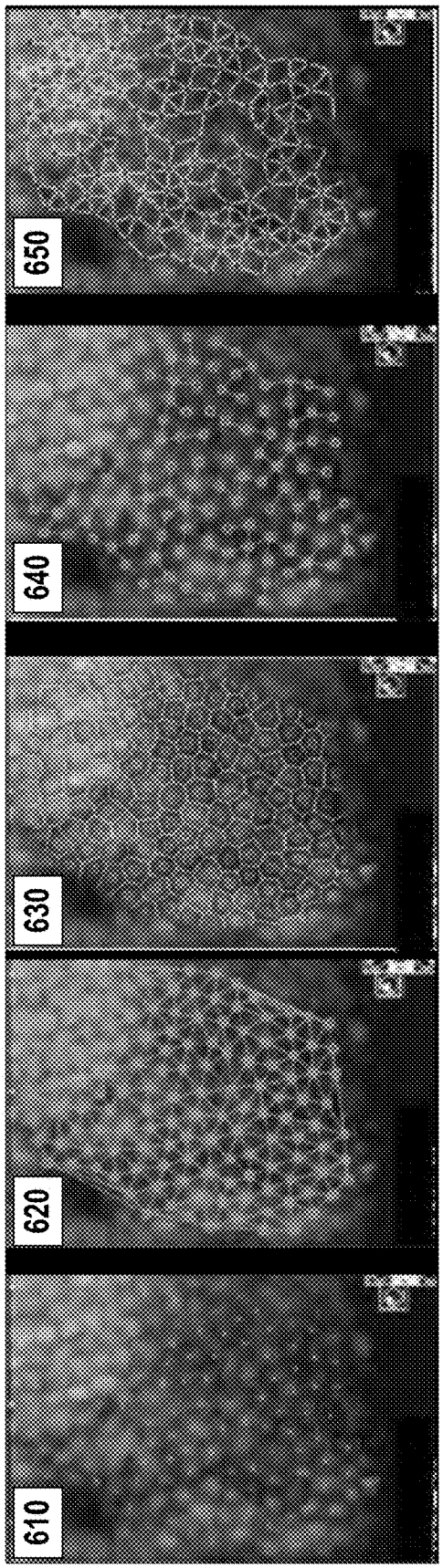
FIG. 6 illustrates example images showing four types of graph structures that can be employed to capture cell arrangement, in connection with various embodiments discussed herein.
Figure 7:
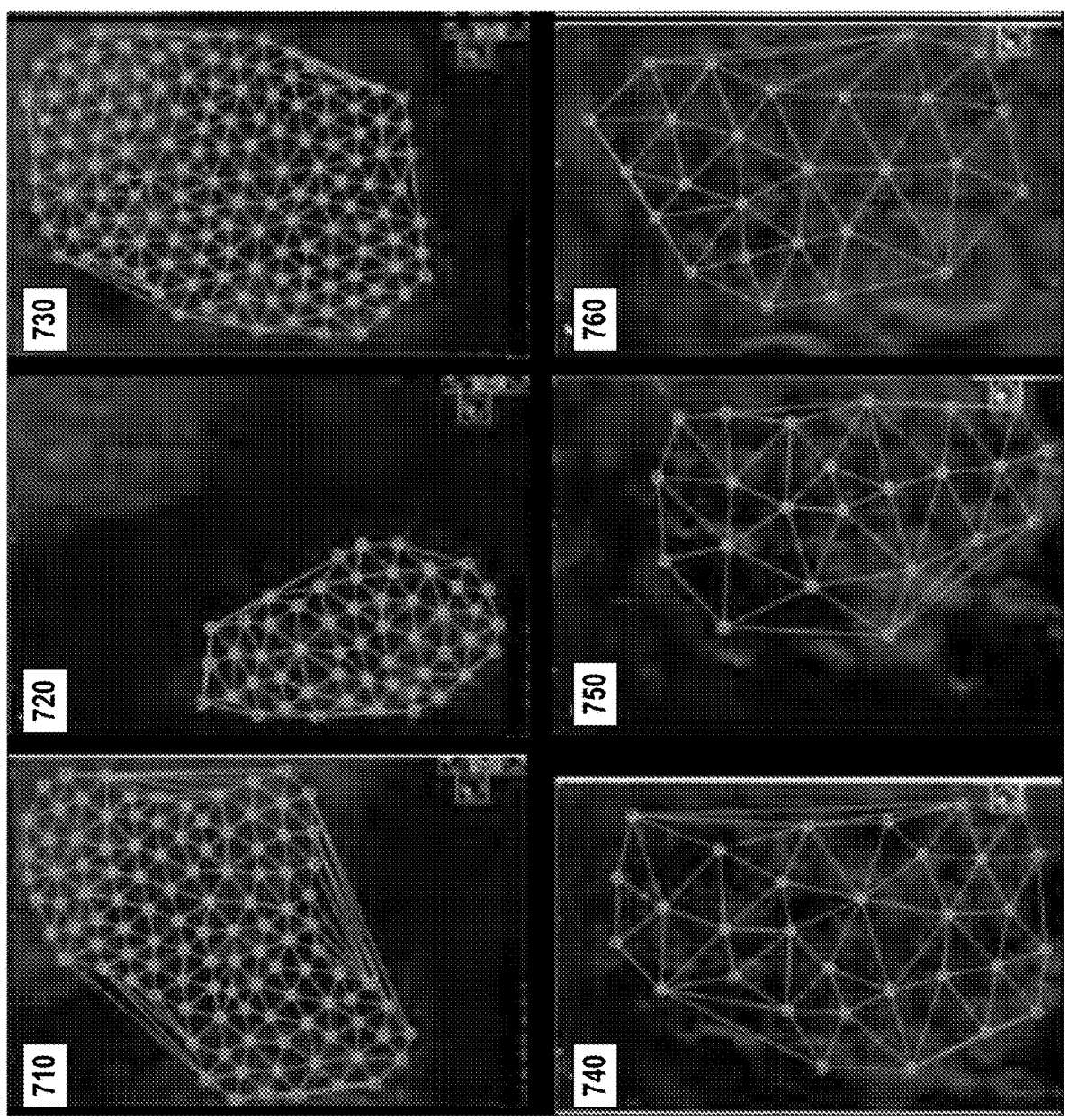
FIG. 7 illustrates example images showing Delauney graph analysis of two groups (top and bottom rows) with clear differences of centrally located, repeated EC images, in connection with various aspects discussed herein.
Figure 8:
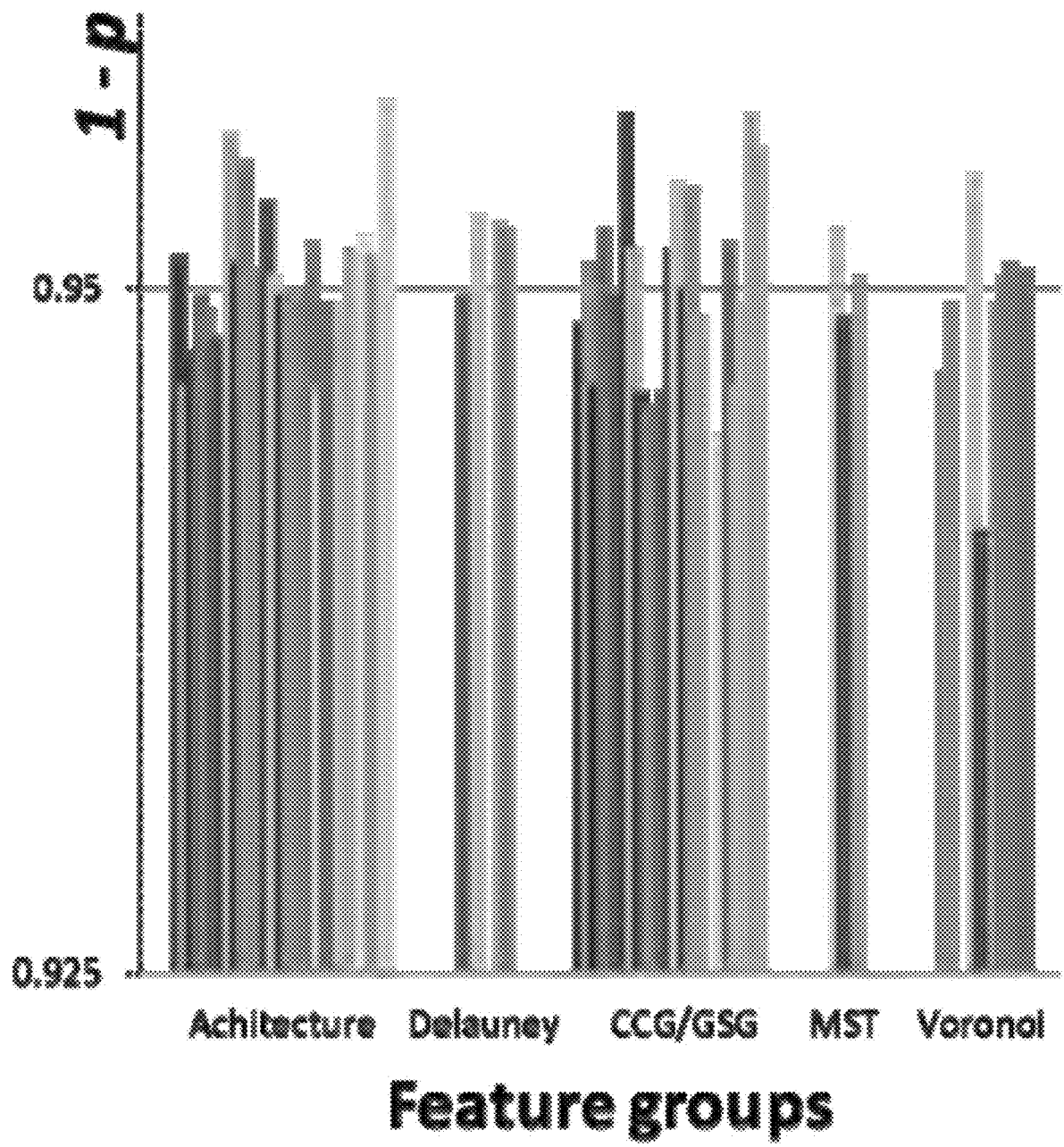
FIG. 8 illustrates a graph showing statistically different features (those above the 0.95 line) as computed from two sets of repeated, central EC images as in FIG. 7, in connection with various aspects discussed herein.
Figure 9:
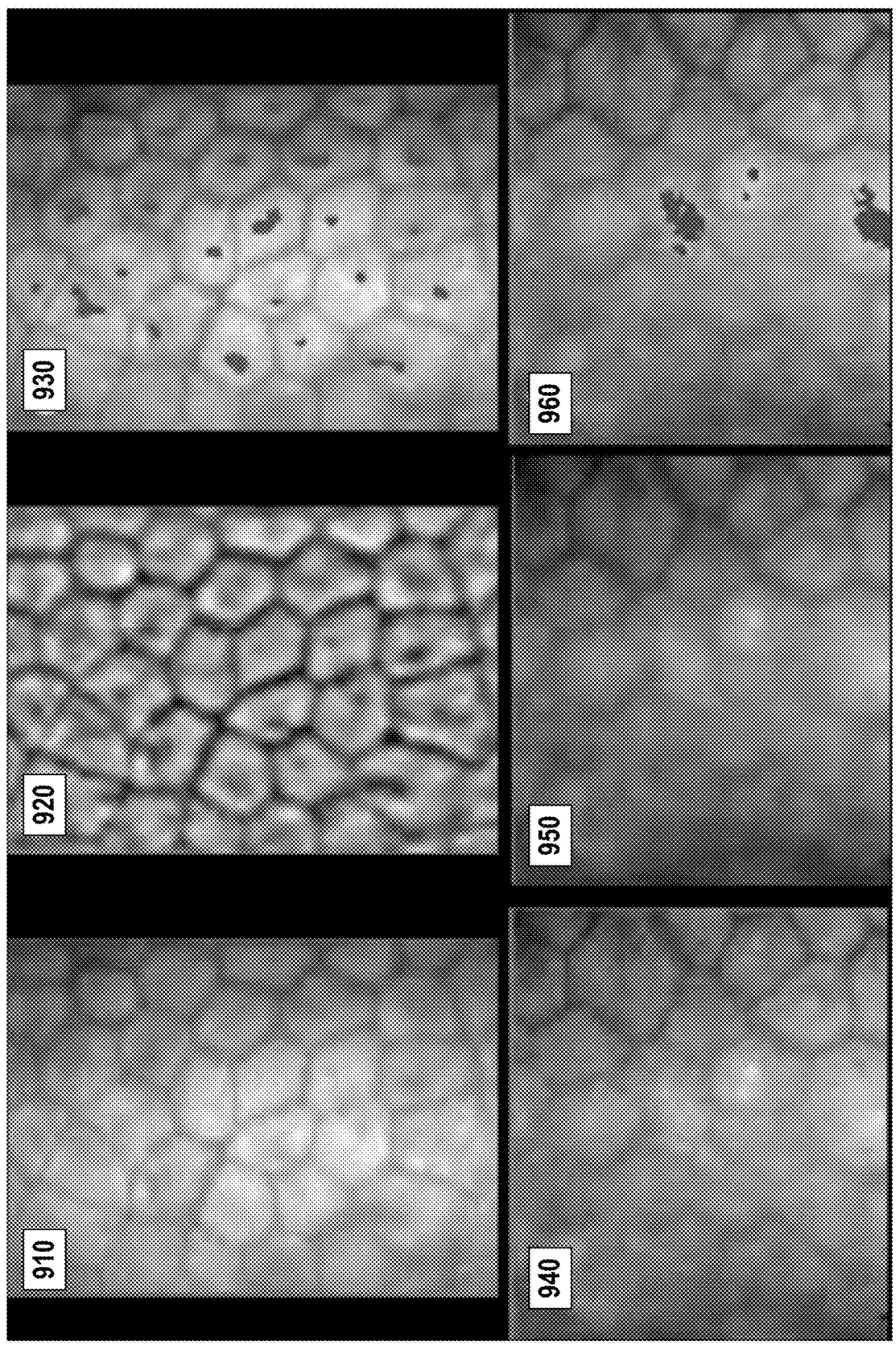
FIG. 9 illustrates images showing image processing to identify dark nuclei and bright pigments in EC images, in connection with various aspects discussed herein.
Figure 10:
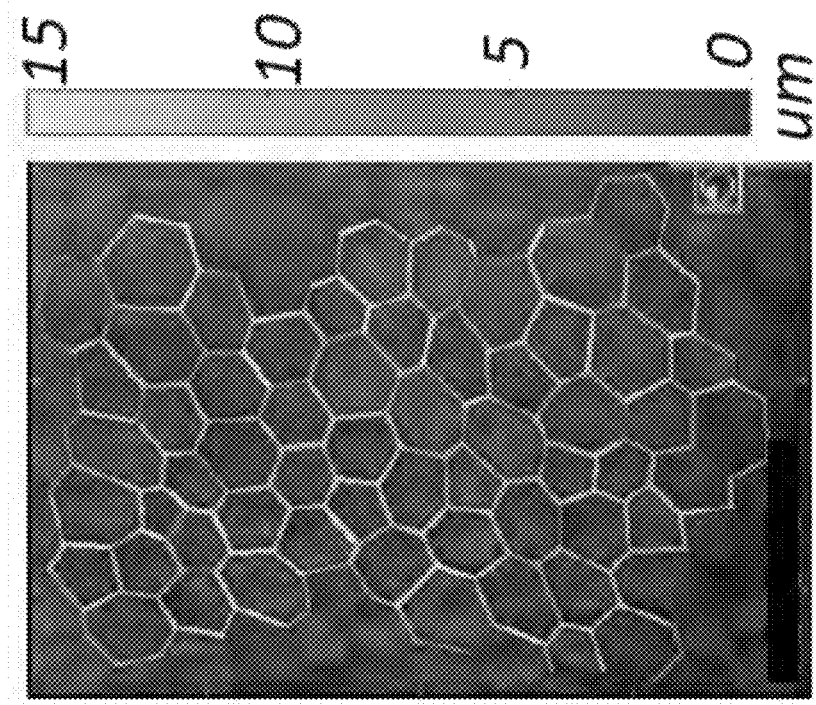
FIG. 10 illustrates a graph and heatmap of an example EC image showing variations in thickness of dark gaps between cells, measured via the full width at half-intensity-minimum of the curve (left), in connection with various aspects discussed herein.
Figure 10:
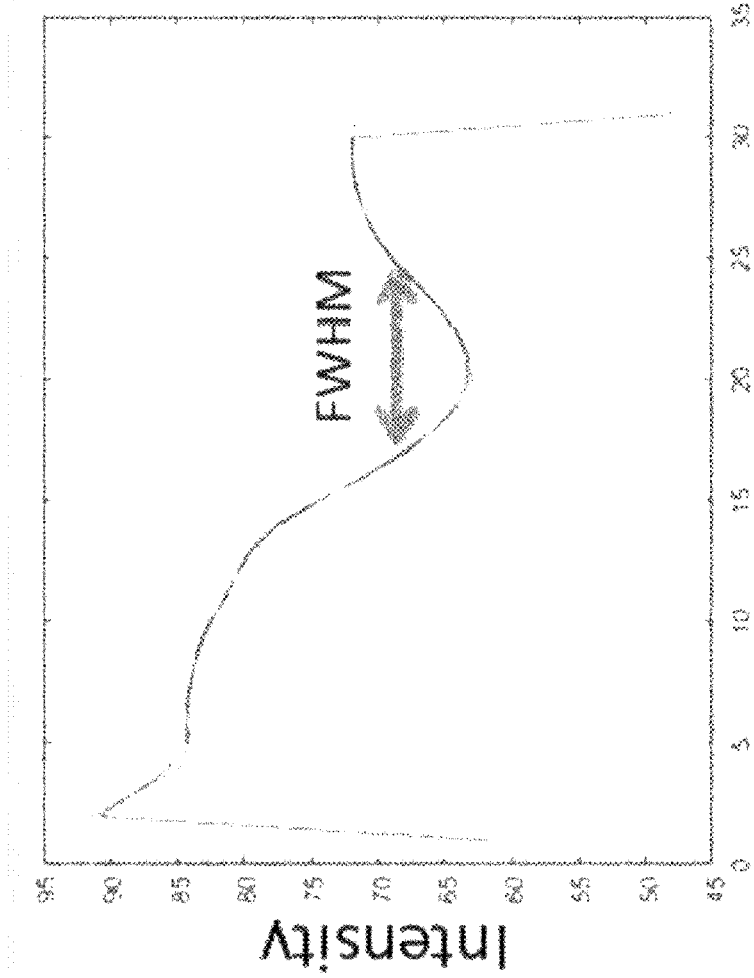
Figure 11:
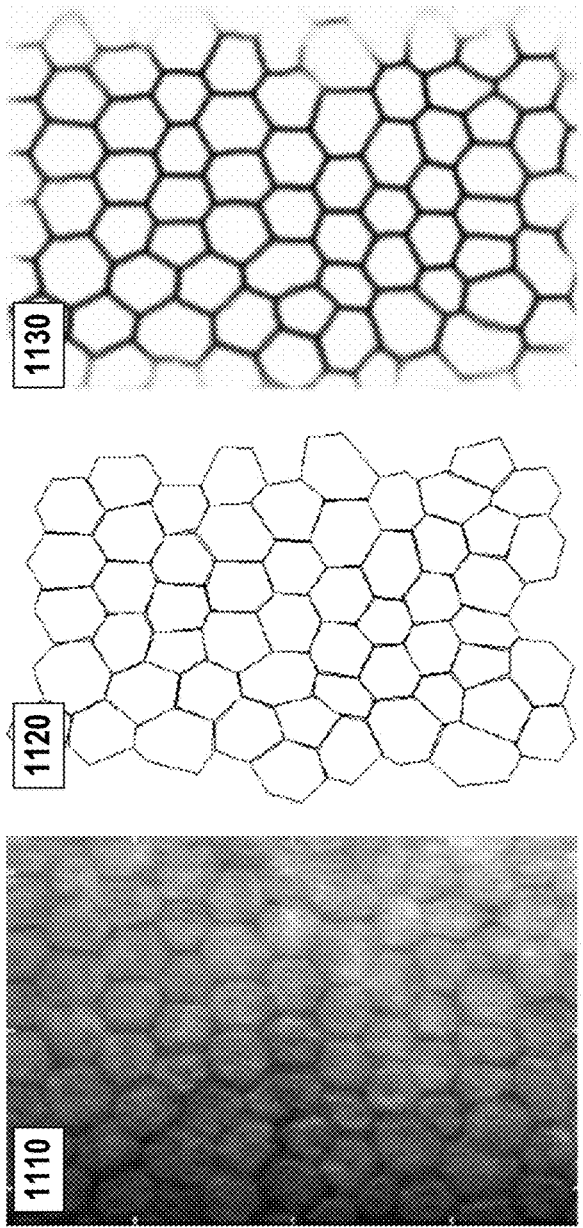
FIG. 11 illustrates example images associated with a post-processing pipeline of the example use cases, in connection with various aspects discussed herein.
Figure 12:
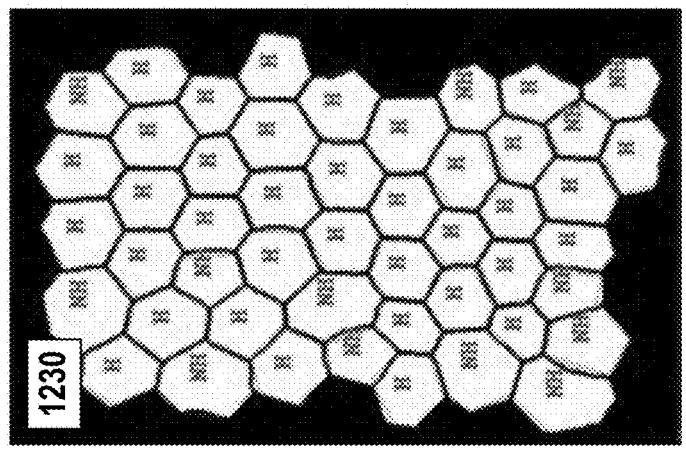
FIG. 12 illustrates example images showing hexagonality determined based on shape detector techniques of the example use cases, in connection with various aspects discussed herein.
Figure 12:
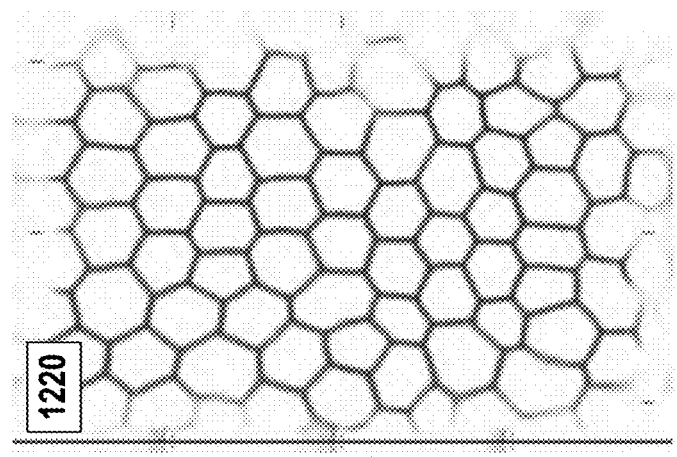
Figure 12:
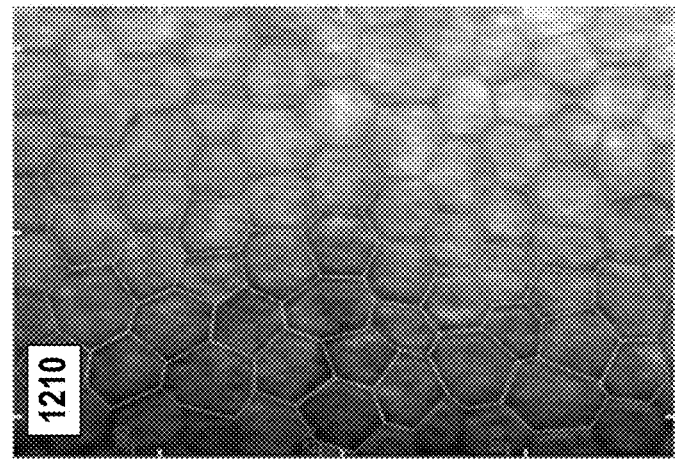
Figure 13:
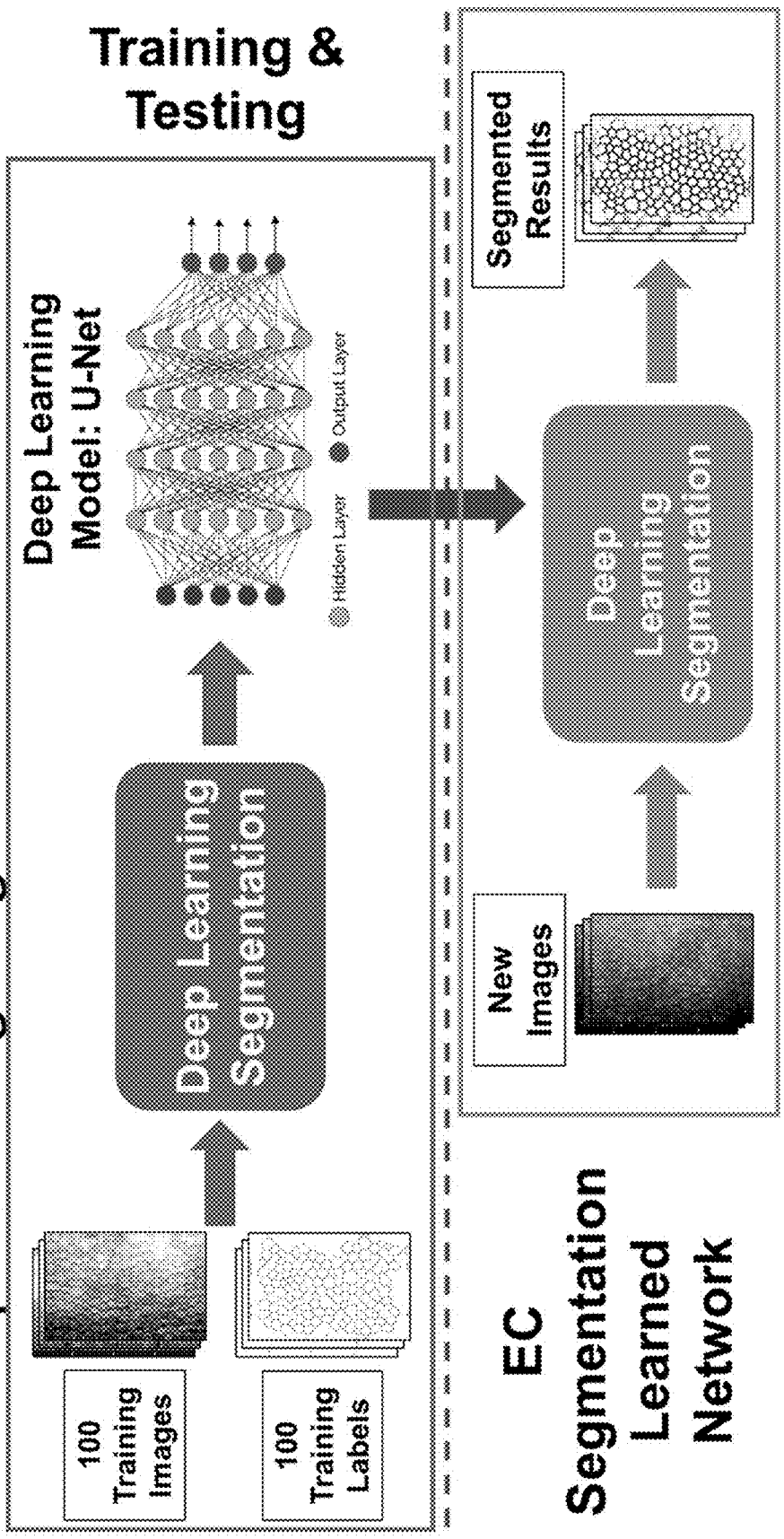
FIG. 13 illustrates a diagram showing an overview of training, testing, and application of the deep learning model for endothelial cell segmentation, in connection with various aspects discussed herein.
Figure 14:
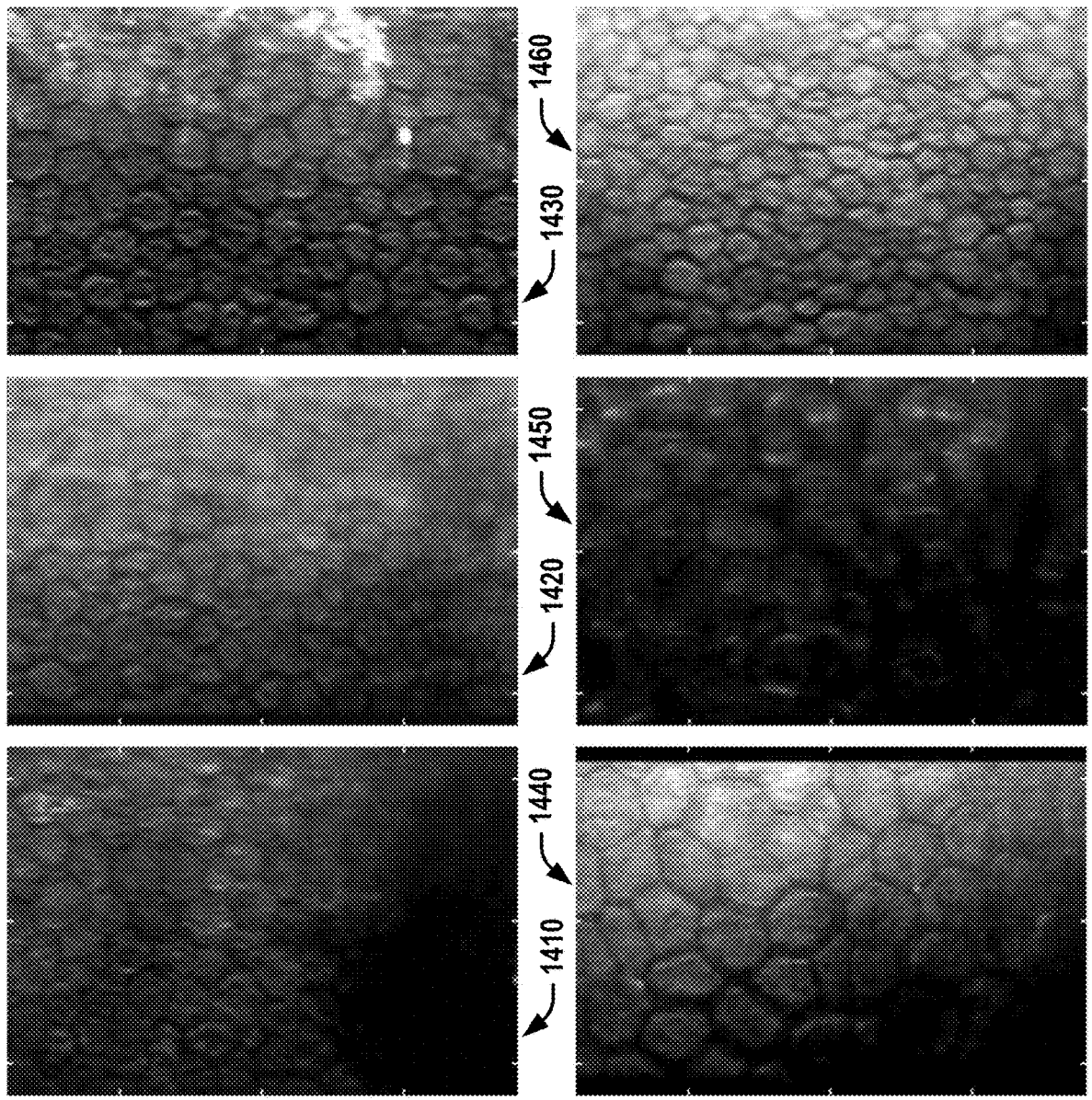
FIG. 14 illustrates specular microscopy images with varying endothelial cell density, duration post-transplant, and contrast from left to right across the image area, in connection with various aspects discussed herein.
Figure 15:
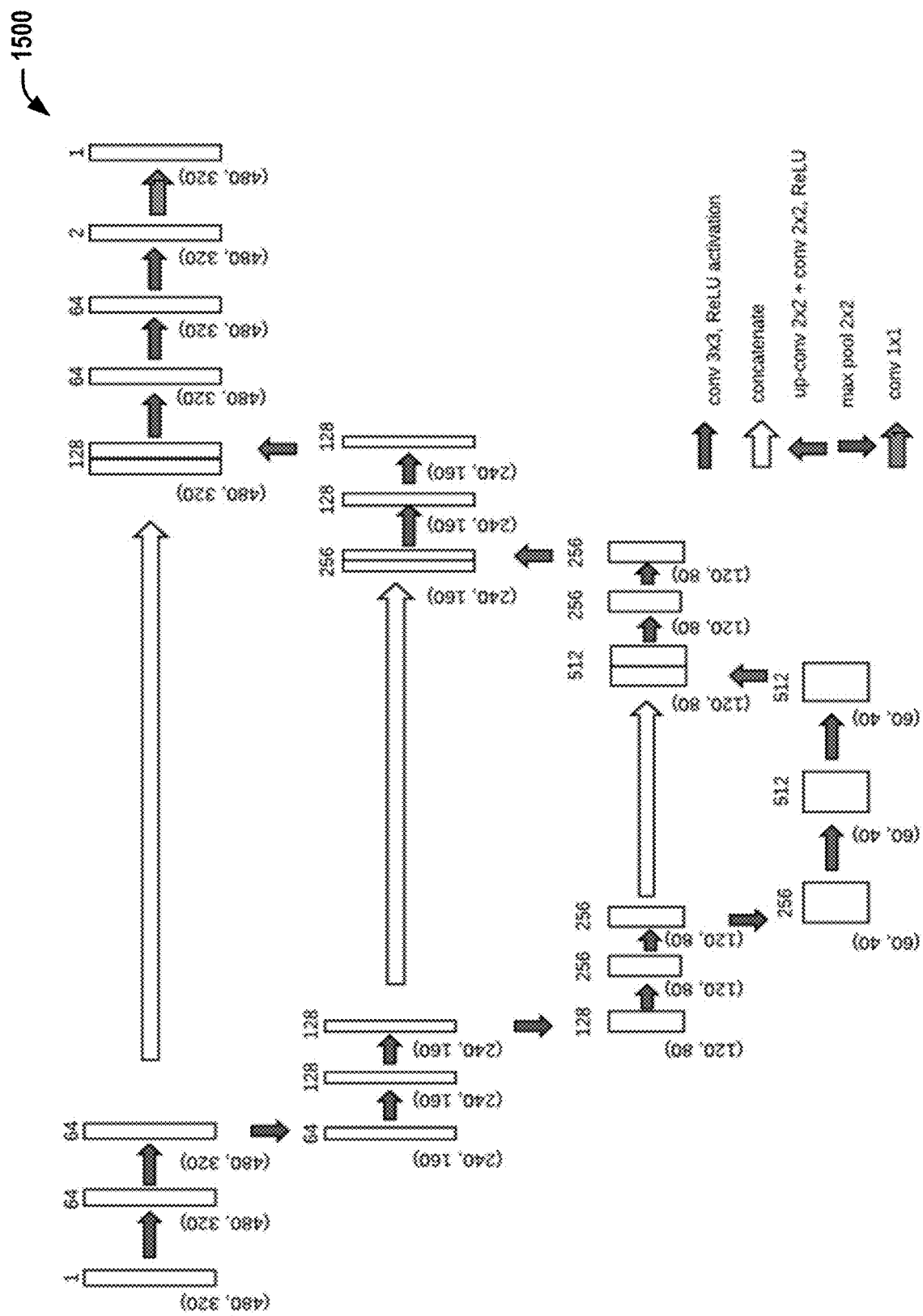
FIG. 15 illustrates a diagram showing the U-Net architecture that can be employed in connection with various aspects discussed herein.

FIGS. 5-30, discussed in greater detail below, show example images, graphs, and other information in connection with the first example use case. FIGS. 5-12 relate to preliminary results during an initial stage of the first example use case. FIG. 5 shows changes in EC images between 0.5-3 years as cells are lost after PK. Although the 6-month image shows good cell density, there is disarray (at 510) as compared to the very regular hexagonal structure in a normal EC layer (not shown). Among other features, the first example use case used four types of graphs to capture cellular structural relationships, as shown at FIG. 6. Delaunay graphs give clear visual and quantitative differences between sets of repeated images in FIG. 7. For these same sets of images, preliminary analysis found that 32 of 80 features were statistically different (FIG. 8). Various embodiments can employ these features or other features determined to have feature stability, a highly desirable property, across repeated images. Initial analysis also noted many visual attributes of EC images that are not captured by existing quantitative biomarkers (ECD, HEX, CV). The first example use case quantitatively assessed dark nuclei and bright pigments (FIG. 9) as well as thickness of dark gaps between cells (FIG. 10), using preliminary image processing algorithms. Visual assessments of such attributes have been related to keratoplasty rejection by the consultants. FIGS. 11-12 illustrate techniques for determining cell density and hexagonality (HEX). FIGS. 13-15 illustrate deep learning techniques for segmenting ECs.

Automated Segmentation of Endothelial Cells

The automated image processing pipeline to generate segmentations of endothelial cells from the first example use case comprised three main steps. First, images were pre-processed to correct for shading/illumination artifacts. Second, a learning algorithm was trained to generate pixel-wise class probability maps. Finally, thresholding and morphological processing operations were performed to generate the final binary segmentation maps. Each of these steps is described in detail below.

EC images, especially specular microscopy images, are commonly associated with varying illumination across the imaging area. The first example use case corrected this artifact by generating a low-pass background image using a Gaussian blur and dividing the original image with the background image. This resulted in a flattened image with even illumination across the complete field of view.

In recent years, deep learning methods (especially convolutional neural networks (CNNs)) have been extensively used to perform medical image analysis tasks, such as image classification and segmentation. CNN architectures are commonly comprised of convolutional, pooling and up-sampling layers and are trained to minimize a pre-defined loss function. Convolutional layers learn one or more filters, where the weights of the kernel filter are shared across the image. Pooling layers reduce the size of the feature maps allowing the network to be invariant to small translations. Upsampling layers allow the creation of an output probability image with the same size as the input. The U-Net network architecture was used in the first example use case, but techniques discussed herein can be extended to any CNN architecture capable of performing either image segmentation or classification tasks.

U-Net was initially shown to segment neuronal structures in electron microscopy (EM) stacks with low pixel errors. Since EC images are visually similar to such stacks (both contain dark cell border regions between brighter cell regions), it was hypothesized that the network would perform well for the task of EC segmentation. The network uses skip connections to recover the full spatial resolution in its decoding layers, allowing one to train such deep fully convolutional networks for semantic segmentation. In initial experiments for the first example use case, the network was trained in a ten-fold cross validation fashion over 100 images and tested on a held-out data set of 30 images. Results from the network on images from the held-out test set are shown in FIG. 19 and other figures. Dice and Jaccard coefficients obtained for U-Net using a fixed threshold and an adaptive threshold are in table 1, below.

TABLE 1

Dice and Jaccard coefficients for CNNs and thresholding techniques
Cell Basis

| Metric | Minimum | Average | Maximum | Std. Dev. |
|---|---|---|---|---|
| Dice Coefficient | 0.00 | 0.87 | 0.98 | 0.17 |
| Jaccard Coefficient | 0.00 | 0.80 | 0.96 | 0.18 |

Finally, the probability maps from the neural network were binarized using one of two methods: adaptive Otsu thresholding over a neighborhood ⅛th the size of the input image or a simple [7×7] sliding window local thresholding approach. In the resulting binary image, predicted cell borders are labeled white (255) and other regions labeled dark (0). A series of morphological operations are performed on the binary images to create thin strokes between cells and to clean the results. Details of the morphological operations are described in the section below.

Automated Determination of Existing EC Metrics

After obtaining segmentation results, the post-processing pipeline involves binarization, skeletonization, and morphological cleaning. Binarization was conducted via an adaptive Otsu threshold. The adaptive threshold was calculated using Otsu's threshold selection method within a sliding window approximately ⅛th the size of the segmentation resulting image. The binarized image was inversed so the end product is white cell borders with black cells and surrounding area. In other aspects, binarization can be obtained via an adaptive threshold. The adaptive threshold was calculated within a sliding window at each pixel location using the following equation: $T=m[1+k(\sigma/\sigma_{dyn}-1)]$, where T is the adaptive threshold value, m is the mean intensity in the pixel neighborhood, $\sigma$ is the standard deviation in the same neighborhood, $\sigma_{dyn}$ is the difference between the maximum and minimum standard deviation across the image, and k is a tunable parameter of the thresholding algorithm. After either technique for thresholding, the binarized image was inverted so the output comprised white cell borders with black cells and surrounding area.

Four consecutive morphological operations were employed in the example used case to create thin strokes between cells and to clean the binarized result. First, a morphological closing operation with a structuring element comprising a disk with radius 4 was performed to close cell borders with gaps from the binarization process. Second, the result was processed with a thinning operation. Thinning results in 1-pixel wide cell borders, thereby matching the width in the ground truth labels. Third, a flood-fill operation was applied, delineating all cells and borders white, and the surrounding area black. This process left small erroneous cell border segmentations outside the primary segmentation regions. A morphological area opening operation was performed that identified and removed 4-connected pixels or any connected components less than 50 pixels. Finally, this image was multiplied by the inverse of the image produced after the second manipulation. The result was a binary image with only the cell area pixels white, and all cell border and surrounding pixels colored black. An example of a raw image, its ground truth segmentation, the automated segmentation result, the binarized segmentation, and the skeletonized binary image are shown in FIG. 13.

In various embodiments, minor segmentation errors can result due to especially challenging areas within a given image or rare cell and cell border cases. To improve the automatically generated segmentations, Guided Manual Correction Software was developed in connection with the first example use case, and can be used to edit the binarized segmentations. Briefly, this software allows one to view multiple images related to the automatic segmentation. The software highlights cells within the binarized segmentation that are deemed to have been segmented incorrectly by the automatic segmentation algorithm. The user then can erase or edit the cell borders utilizing built-in tools within the software. The final edited binarized segmentation will be used in subsequent processing. The algorithm for identifying potential segmentation errors is based upon deep learning probability outputs and cell areas. The Guided Manual Correction Software is discussed in greater detail in co-owned U.S. Provisional Patent Application No. 62/985,481, filed Mar. 5, 2020, and entitled "AUTOMATED SEGMENTATION AND GUIDED CORRECTION OF ENDOTHELIAL CELL IMAGES," the contents of which are herein incorporated by reference in their entirety.

To obtain the ECD from the skeletonized binary segmentation result, the total cell area was calculated by automatically counting the total number of pixels the cell area (including the cell borders) and multiplying this by the area of one pixel (0.65 um$^2$). The area of one pixel is obtained from the corresponding microscope's calibration measurements. Then a connected components tool was used to identify every cell in the region of interest; two area thresholds were used to remove the background area (>6500 um$^2$) and regions that were unrealistically small for cells (<65 um$^2$). The remaining cells were counted and noted. The ECD for each image is the number of cells divided by the total area of the cell sample region of interest.

CV calculations start with using connected components and area thresholds to identify true cells in the region of interest. Then the area of each cell was calculated individually including its border. Outliers were removed from the list of cell areas as these are the result of improper cell closings during the segmentation and post-processing steps. The standard deviation and mean of the individual cell areas are calculated, and the ratio of these two values represent the CV.

To determine the HEX value of an image, a shape detection algorithm is used to identify hexagonal versus non-hexagonal cells. The skeletonized image mentioned previously is inverted, then the white borders were dilated by 2 pixels, and finally reversed again so that the final image has white cell area with black thick borders and black surrounding area. The shape detection algorithm utilized in the first example use case was based on the Ramer-Douglas-Peucker algorithm, which takes a set of points in a curve, and reduces the points to define a similar curve or line with less points, and is applied to the cell borders. Using a contour approximation, vertices were defined at the end of these curves/lines. The number of vertices per shape, or cell in this case, are counted, and if there are 6 vertices, the cell is labeled a hexagon; if there are not 6 vertices, the cell is labeled non-hexagon. HEX equals the number of hexagonal cells divided by the total number of cells in region of interest. FIG. 14 displays an example result of this shape detection algorithm.

Determination of Other Cellular Features

Hundreds of other features were computed from the segmented EC images. First, the structure of cellular arrangement was captured using graphs. Graph analytics were applied (e.g., Delaunay and cell cluster graphs, and their computed features, as shown in FIGS. 6-8). Graph analytic features comprises features for each node and/or global features. As there are a very large number of potential features, various feature selection techniques (e.g., minimum-redundancy-maximum-relevance (mRMR), etc.) were applied to identify the ones most important for determining corneas at risk. Second, cellular architectural morphometric measures were computed from single cells (e.g., area and eccentricity, etc.), in many cases using existing library computer functions. Third, a variety of hand-crafted features targeting image attributes in the literature were computed (e.g., architecture features shown in FIG. 8). These features were developed based upon image attributes related to rejection (e.g., irregular cell morphology, irregular distribution, cell nuclei, cellular reflectivity, wall thickness, etc.). Additionally, examples of new measures (wall thickness, bright pigment, and dark nucleus) are illustrated in FIGS. 9-10. For most features, statistical measures over the image (e.g., mean, standard deviation, skewness, kurtosis, and/or binned histogram, etc.) were extracted.

Determination of Corneas at Risk

Machine learning classifiers were trained on large sets of data which include EC images as well as outcomes (e.g., rejection, failure or no adverse event) and used for validation on held-out test sets. Software developed for the first example use case segments ECs, extracts features as discussed above, and predicts from the EC images those cornea(s) that will experience a rejection episode or future graft failure. In addition to predicting keratoplasty outcome, various embodiments can evaluate rate of cell loss and time to event as a secondary outcome. Machine learning classifiers and classification results of various embodiments can provide highly accurate results, based on training and testing on more than 6,000 well-curated EC images obtained at multiple time points from already-collected corneal datasets, including SMAS (EY12728) applied to penetrating keratoplasty (PK) at CWRU, CPTS (EY020798) applied to Descemet stripping automated endothelial keratoplasty (DSAEK) at CWRU, and corneal EC images from the Netherlands Institute for Innovative Ocular Surgery, hereafter called CNIIOS, applied to Descemet membrane endothelial keratoplasty (DMEK).

Details.

The actual classifiers can be created using support vector machine (SVM), random forest, or any number of other classification methods (e.g., a Linear Discriminant Analysis (LDA) classifier, a Quadratic Discriminant Analysis (QDA) classifier, etc.). Classifiers were built on images from multiple time-points simultaneously, 6-month post-keratoplasty images, and serial time-point images. To reduce the total number of features and improve generalizability, techniques for feature reduction were employed. Feature reduction methods (for example, minimum redundancy maximum relevance (mRMR)) were applied to reduce the number of features considered and to possibly suggest features for potential additional refinement. Another dimensionality reduction approach would be to use a Cox Proportional Hazards Model (CPHM) or the Wilcoxon rank-sum test to determine features most indicative of a future adverse event (rejection or failure). Performance was assessed using cross-validation experiments and the number of trials was increased by rotating fold membership. Classifiers can be tuned appropriately. Since the number of no-adverse events greatly exceeds the number of rejection episodes and graft failures in the datasets, steps can be taken for training with imbalanced data. Feature stability was assessed across the 3 image repeats using intra-class correlation coefficient and optionally a latent instability score championed by others. If deemed appropriate, a second feature stability test was run comparing good and fair quality images routinely labeled by CIARC. In other embodiments, deep learning techniques can be employed in place of machine learning classifiers to distinguish EC images between no-adverse event vs. failure and/or no-adverse event vs. non-rejection failure vs. rejection.

Additional work in connection with the first example use case comprises collecting over 900 images from the NIIOS dataset. Based on these images, automatic and guided cell segmentation can be conducted. Based on the segmented images, features can be calculated, which can comprise standard features, graphical features, and/or novel features. From the calculated features, classification experiments can be performed on the EC features to determine the ability to classify keratoplasties prone to rejection.

FIGS. 5-27, discussed below, show example images, graphs, and other information in connection with the first example use case.

Referring to FIG. 5, illustrated are serial specular microscope imaging following a PK procedure, in connection with various aspects discussed herein. Images 510-540 were taken at 6 months, 1 year, 2 years, and 3 years, respectively, and show a continuing decrease (2684, 2027, 1430, 1184 cells/mm$^2$, respectively) in cell density. This eye later became dysfunctional. Notably, although there is a high density of cells at 6 months, there is variation in cell size and irregular non-hexagonal arrangement, showing disarray as compared to the very regular hexagonal structure in a normal EC layer. Various embodiments can predict eyes at risk from such images using machine learning.

Referring to FIG. 6, illustrated are example images showing four types of graph structures that can be employed to capture cell arrangement, in connection with various embodiments discussed herein. Cell centers were marked in the EC image 610. In 620-650, the graphs shown are Delauney, Voronoi, minimum spanning tree (MST), and cell cluster graph (CCG), respectively. Many computational features were computed from the graphs, for example, average area from Voronoi, average eccentricity from cell cluster graph, standard deviation of edge length from MST, etc.

Referring to FIG. 7, illustrated are example images showing graph analysis of two groups (top and bottom rows) of centrally located, repeated EC images, in connection with various aspects discussed herein. Delauney graphs show clear visual differences between the two groups. Features from the graphs showing statistically significant differences ($p<0.05$, as shown in FIG. 8) included standard deviation of triangle area from Delauney, average chord length from Voronoi, disorder of edge length from MST, and percentage of isolated points from CCG.

Referring to FIG. 8, illustrated is a graph showing statistically difference features (those above the 0.95 line) as computed from two sets of repeated, central EC images as in FIG. 7, in connection with various aspects discussed herein. Features shown in FIG. 8 were computed from 4 graph types (as in FIG. 6) and from tissue architecture (e.g., average distance to 7 nearest neighbors, although a different number of neighbors can be used in various embodiments). A permutation test was used to evaluate significance. Of the 80 features in the categories of FIG. 8 that were evaluated, 32 were significantly different ($p<0.05$) and more were nearly significant. FIG. 8 shows examples of features that can be created that show differences between groups of EC images. One criterion for good features is stability across repeated images, and additional, less preliminary results are discussed below. Various embodiments can employ any of a variety of features discussed herein for classification of EC images (e.g., as normal vs. failure risk, or normal vs. non-rejection failure risk vs. rejection risk, etc.).

The first example use case identified many visual attributes of EC images that are not captured by existing quantitative biomarkers (ECD, HEX, CV). Referring to FIG. 9, illustrated are images showing image processing to identify dark nuclei (910-930) and bright pigments (940-960) in EC images, in connection with various aspects discussed herein. For dark nuclei, starting with segmented cells, intensity background variation was corrected and noise reduced (920, 950), and conditional dilation was applied to a threshold. Small regions were removed. Bright pigments (940-960) were processed similarly. Referring to FIG. 10, illustrated are a graph and heatmap of an example EC image showing variations in thickness of dark gaps between cells, in connection with various aspects discussed herein. On the right of FIG. 10 is shown a heatmap of "dark gaps" between cells. Starting with segmented cells, the full width of the half-intensity-minimum of the curve was measured, as shown on the left of FIG. 10. The curve is an average of 11 perpendicular lines extracted from the midway point of a side. Gaps can be accentuated by lateral distances as well as potentially cell height in these obliquely illuminated images. Visual assessments of attributes such as those shown in FIGS. 9-10 have been related to keratoplasty rejection by the consultants.

FIGS. 11-12 show techniques related to determining endothelial cell density (ECD) and hexagonality (HEX). Referring to FIG. 11, illustrated are example images associated with a post-processing pipeline of the first example use case, in connection with various aspects discussed herein. FIG. 11 shows the following in connection with a post-processing pipeline for an example image: (a) Corneal endothelium image captured via specular microscopy at 1110; (b) ground truth segmentation at 1120; (c) U-Net segmentation probability result at 1130; (d) binarized segmentation at 1140; and (e) skeletonized segmentation at 1150. Referring to FIG. 12, illustrated are example images showing hexagonality determined based on techniques of the first example use case, in connection with various aspects discussed herein. FIG. 12 shows the following results: (a) Corneal endothelium image and corner analysis with borders in green at 1210; (b) probabilities from the deep neural network at 1220; (c) results of algorithm on binarized network outputs with H=hex and NH=non-hex at 1230.

Referring to FIG. 13, illustrated is a diagram showing an overview of training, testing, and application of the deep learning model for endothelial cell segmentation, in connection with various aspects discussed herein. The deep learning segmentation algorithm in the first example use case started with 100 EC images and corresponding manual annotation labels to train a deep learning network called U-Net. U-Net can learn features from the training images and labels so it can classify a pixel as either cell border, or cell and surrounding area. Once trained, additional EC images (e.g., from a test set, patient imaging, etc.) can be provided to the EC segmentation learned network to generate segmented results. For the first example use case, of 130 EC images, 30 were in the held out test set, and the remaining 100 were used with 5-fold cross validation to train the model for subsequent testing on the 30 held out test images.

Referring to FIG. 14, illustrated are example specular microscopy images 1410-1460 with varying endothelial cell density, duration post-transplant, and contrast from left to right across the image area, in connection with various aspects discussed herein.

Referring to FIG. 15, illustrated is a diagram showing an example U-Net architecture that can be employed in connection with various aspects discussed herein. In FIG. 15, the numbers on top and the left bottom corner of each tensor indicate the number of channels/filters and its height and width respectively. The network comprises multiple encoding and decoding steps with three skip connections between the layers (white arrows). The remaining arrows are as follows: the blue rightward arrow is a convolution with (3, 3) filter size, ReLU activation; the upward arrow is an up-convolution with a (2, 2) kernel using max pooling indices from the encoding layers; the downward arrow is a max pooling with a (2, 2) kernel; and the pink rightward arrow with a "1" in the arrowhead is a (1, 1) convolution with sigmoid activation.

Figure 16:
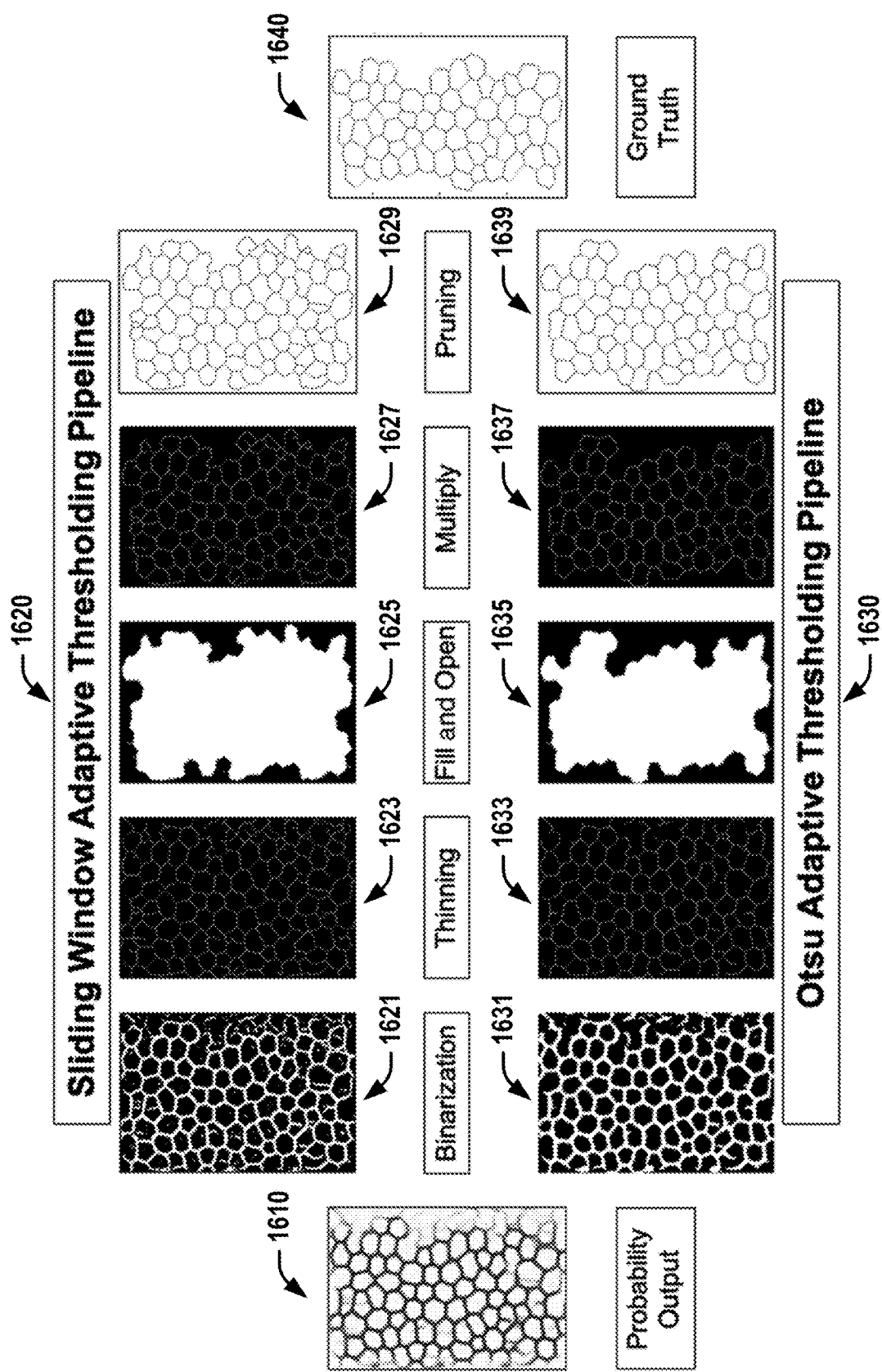
FIG. 16 illustrates images showing two different thresholding techniques that can be employed to convert probability outputs to binarized outputs, followed by a post-processing pipeline consisting of four morphological operations, in connection with various embodiments.

Referring to FIG. 16, illustrated are images showing two different thresholding techniques that can be employed to convert probability outputs to binarized outputs, in connection with various embodiments. Sliding window adaptive thresholding (1620, comprising 1621-1629) and adaptive Otsu thresholding (1630, comprising 1631-1639) were used to convert probability outputs from the U-Net algorithm (e.g., example probability output image 1610) to binarized, single-pixel width cell borders (e.g., examples 1629 and 1639) which can be compared to ground truth labels (e.g., example ground truth labeling 1640). For adaptive threshold, the steps are: binarization (1621), thinning to obtain single pixel wide lines (1623), filling and opening to remove extraneous branches (1625), multiplication with 1623 to obtain the cells borders that fully enclose cells (1627), and finally pruning to remove small spurious segments (1629). Image 1629 was compared to the ground truth label image 1640 for training and testing. Adaptive Otsu (1630) was processed the same way, at 1631-1639.

Figure 17:
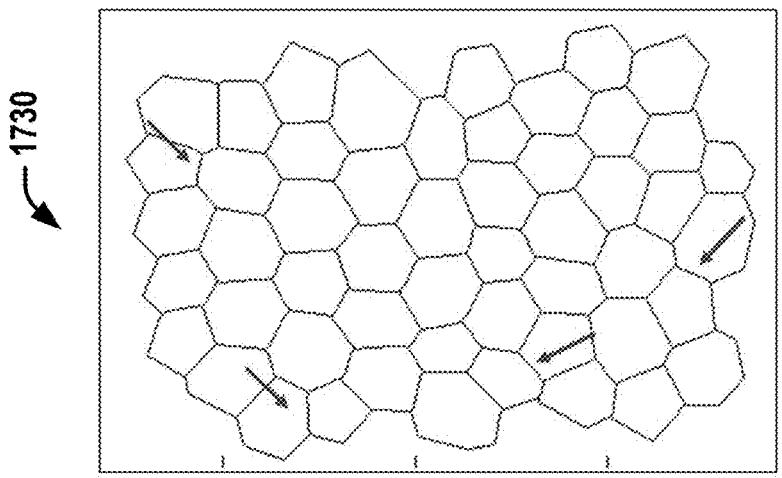
FIG. 17 illustrates images showing an example endothelial cell image, manual cell segmentation analysis, and the corresponding ground truth, corrected for border overlaps, used in the example use cases, in connection with various aspects discussed herein.
Figure 17:
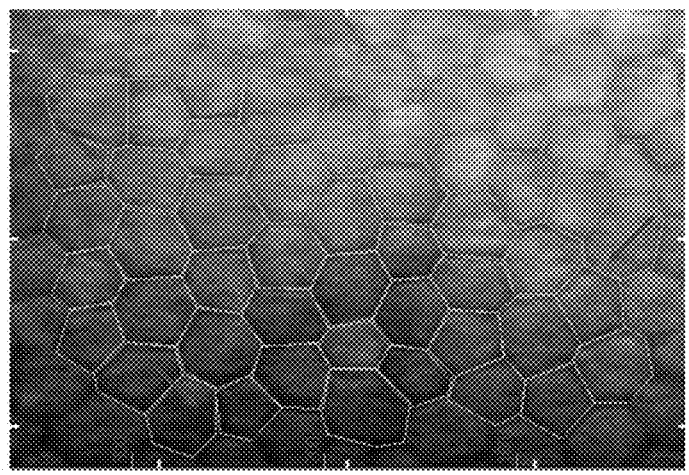
Figure 17:
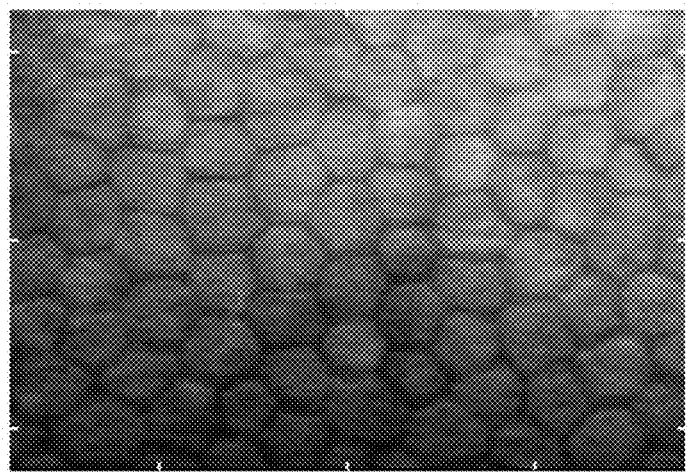

Referring to FIG. 17, illustrated are images showing an example endothelial cell image, manual cell segmentation analysis, and the corresponding ground truth, corrected for border overlaps, used in the first example use case, in connection with various aspects discussed herein. At 1710 is a good quality sample EC image with cells of various shapes and sizes, showing the consistently-obtained brightness variation from left to right. At 1720 is the cell-border segmentation overlay created by an analyst using the HAI CAS software. In this good quality image, segmentations were obtained throughout the image (cells cut-off at the boundaries of the image are not labeled). At 1730 is the binary segmentation map used as a ground-truth label image. The arrows indicate example double borders generated by the HAI-CAS software in 1720 that were replaced with single borders in 1730 following processing).

Figure 18:
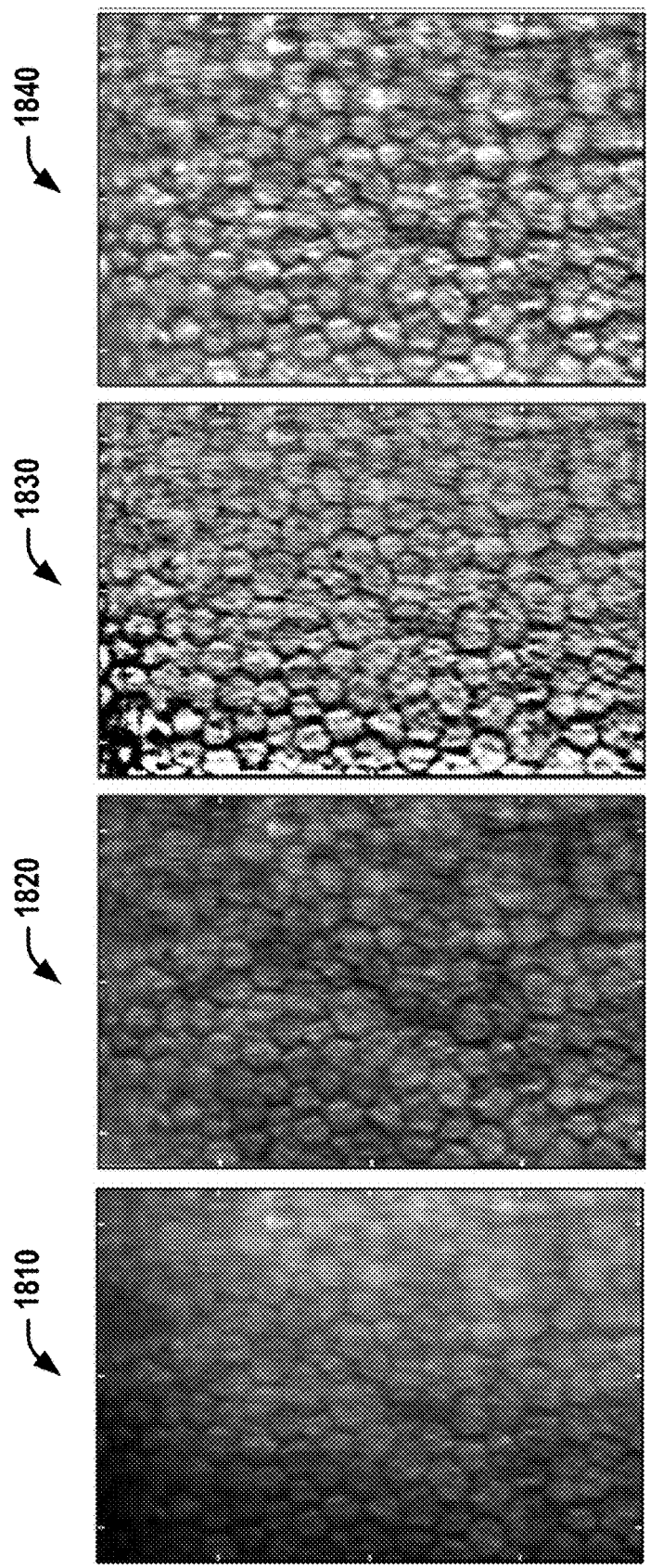
FIG. 18 illustrates example images showing three pre-processing shading correction methods applied to a representative EC image, in connection with various aspects discussed herein.

Referring to FIG. 18, illustrated are example images showing pre-processing shading correction methods applied to a representative EC image, in connection with various aspects discussed herein. The original image 1810 is corrected via localization (1820), division (1830), and subtraction (1840) methods. Each of the correction methods significantly flattened the image. For the division method, a low-pass background image was generated using a Gaussian blur and divided the original image by the background image to create a flattened image. A normalized Gaussian filter with standard deviation σ=21 pixels and a kernel foot print (65×65 pixels) was used, the 99th percentile of the flattened unit 8 image's intensity was set to the maximum intensity (255), and then the rest of the image's intensity was normalized so its distribution expanded the (0 to 255) intensity range. For the subtraction method, a low-pass background image was generated via the same Gaussian blur previously mentioned, and then this background image was subtracted from the original image, wherein the flattened image was normalized using the same method as before. For the localization method, the brightness was normalized along the vertical and horizontal directions by adding the difference between the average image brightness and the average brightness in the corresponding row/column at each pixel. New pixel values were given as $$p'(x, y) = p(x, y) + \left[L - \sum_j \frac{p(x, j)}{H}\right] + \left[L - \sum_i \frac{p(i, y)}{W}\right],$$

where p'(x, y) is the new pixel value, p(x, y) is the original pixel value, L is the average brightness in the image, H is the height of the image, and W is the width of the image.

Referring to FIG. 19A, illustrated are images of deep learning probability maps of an example test image following four types of pre-processing, in connection with various aspects discussed herein. An original test image 1900 was processed with deep learning following no pre-processing 1902, localization pre-processing 1904, division pre-processing 1906, and subtraction pre-processing 1908. In the center of the probability outputs, the borders appear more black due to the high confidence of the trained algorithm in these regions, however, toward the edges and some blurry areas of the original images, the borders appear more gray because the algorithm is less confident here (indicated by arrows).

Referring to FIG. 19B, illustrated are images showing the final segmentation results of the EC image of FIG. 18 with the four pre-processing methods discussed above, according to various aspects discussed herein. At 1950 is the ground truth label. The final segmentation results shown in 1952-1958 are: after no pre-processing (1952), after localization pre-processing (1954), after division pre-processing (1956), and after subtraction pre-processing (1958). The dashed circles indicate correct cell segmentation, whereas the solid circles indicate incorrect cell segmentation. The arrows indicate regions of newly segmented cells not previously annotated.

Referring to FIG. 20A, illustrated are three example EC images (2000, 2004, and 2008) and corresponding segmentation (2002, 2006, and 2010) highlighting cells with differences between manual and automatic segmentations, in connection with various aspects discussed herein. Cell boundaries solely identified via manual segmentation are in green, those identified via both are in yellow, and boundaries solely identified via automatic segmentation are in red. Images 2000 and 2002 shows two examples in white circles where the automated method first split a single cell and then merged two cells into one cell. The reviewers agreed the manual annotations were more accurate than the automated segmentations. Images 2004 and 2006 illustrates an example where the automated method merged two cells into one cell, and the reviewers concluded the case equivocal because it was unclear which method actually segmented the cell correctly. Images 2008 and 2010 shows an example where the automated method split one of the manually annotated cells into two cells. The reviewers considered this case to have been segmented more accurately by the automated method than the manual annotation.

Referring to FIG. 20B, illustrated are three examples of EC images showing the automatic segmentation method identifying and segmenting cells outside of the sample area of the ground truth annotations, in connection with various aspects discussed herein. Images 2050, 2054, and 2058 are sample EC image from the independent held-out test set, and images 2052, 2056, and 2060 show the respective ground truth (green) and automatic (red) segmentations overlaid, showing cells outside of the ground truth sample area segmented by the U-Net algorithm.

Figure 21:
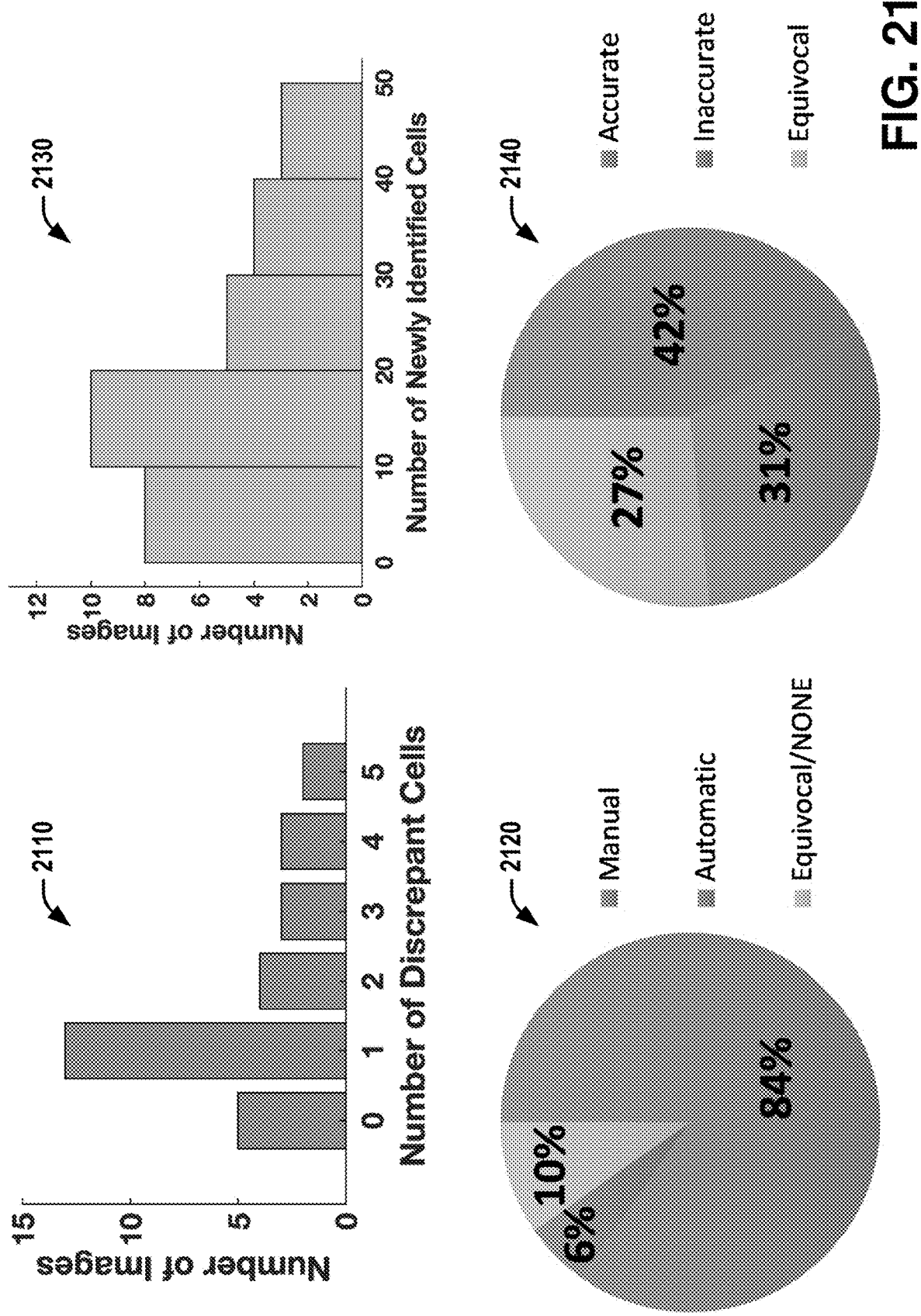
FIG. 21 illustrates charts showing the results of visual analysis of automated cells in a held-out test set comprising 30 images, in connection with various aspects discussed herein.

Referring to FIG. 21, illustrated are charts showing the results of visual analysis of automated cells in a held-out test set comprising 30 images, in connection with various aspects discussed herein. Within the manually analyzed regions, experts identified that only 52 of 1876 cells (3%) required reconsideration. A histogram of numbers of discrepancies are shown at 2110, where 22 images (73%) contained 0, 1, or 2 potential discrepancies. Notably, among discrepancies, the automated result was deemed better or equivocal 16% of the time, giving only 44 (2.3%) of cells where experts deemed it desirable to change the automated result, as seen at 2120. In the regions newly segmented by the automated method, 564 new cells (an increase of 30%) were identified, with the image histogram shown at 2130. Nearly 70% or 390 of newly segmented cells were deemed acceptable (accurate or equivocal in the pie chart at 2140).

Figure 22:
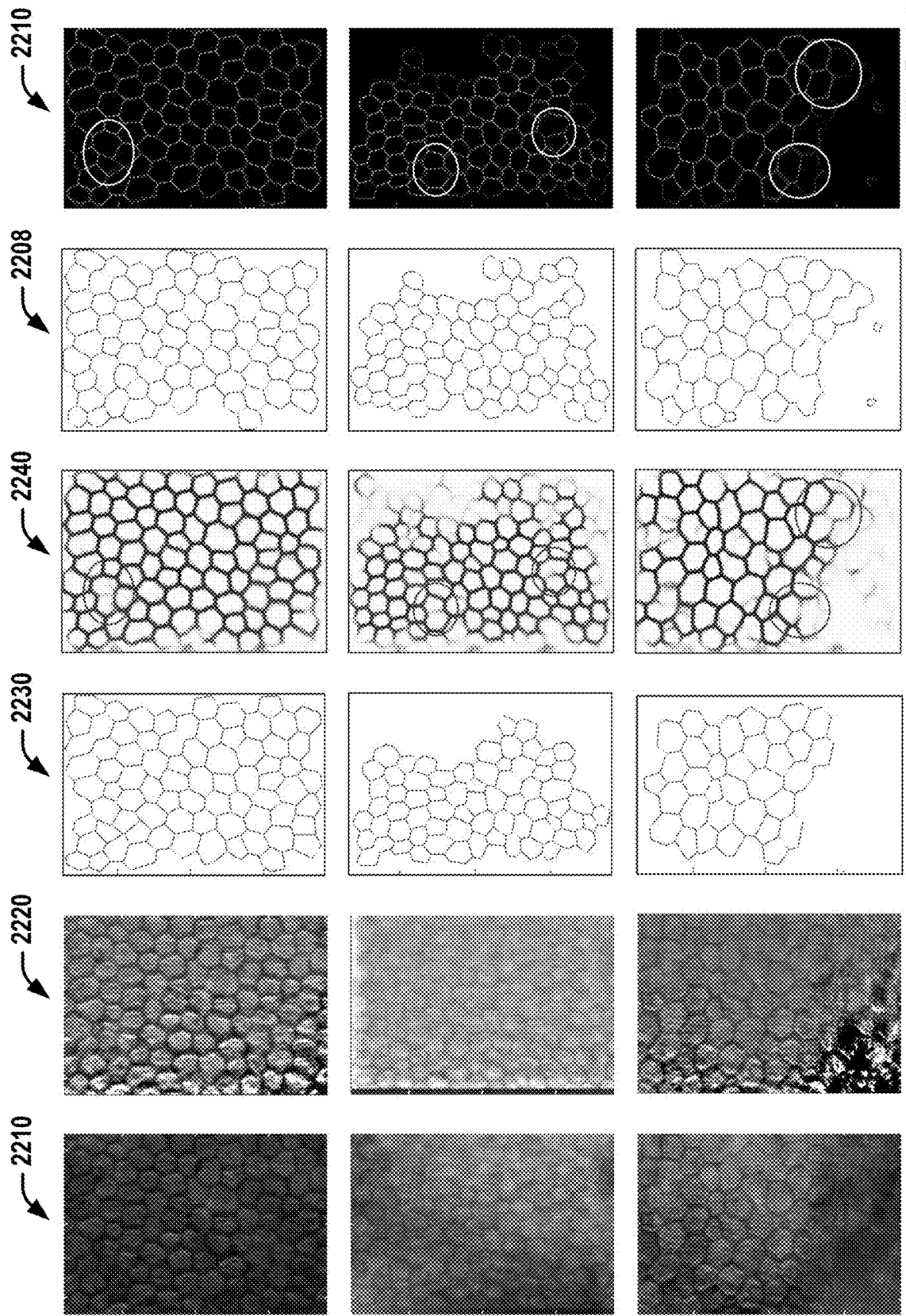
FIG. 22 illustrates images showing three example post-DSAEK EC images (corresponding to the three rows) having undergone both manual and automatic segmentation, in connection with various aspects discussed herein.

Referring to FIG. 22, illustrated are images showing three example post-DSAEK EC images (corresponding to the three rows) having undergone both manual and automatic segmentation, in connection with various aspects discussed herein. Column 2210 shows the original, raw EC images. Column 2220 shows the enhanced, pre-processed EC images. Column 2230 shows the ground truth images corrected. Column 2240 shows the U-Net probability outputs. Column 2250 shows the final border segmentations following post-processing pipeline. Column 2260 shows an overlay of ground truth manual segmentations (green) and automatic segmentations (red). Yellow indicates where the manual and automatic segmentations overlapped.

Figure 23:
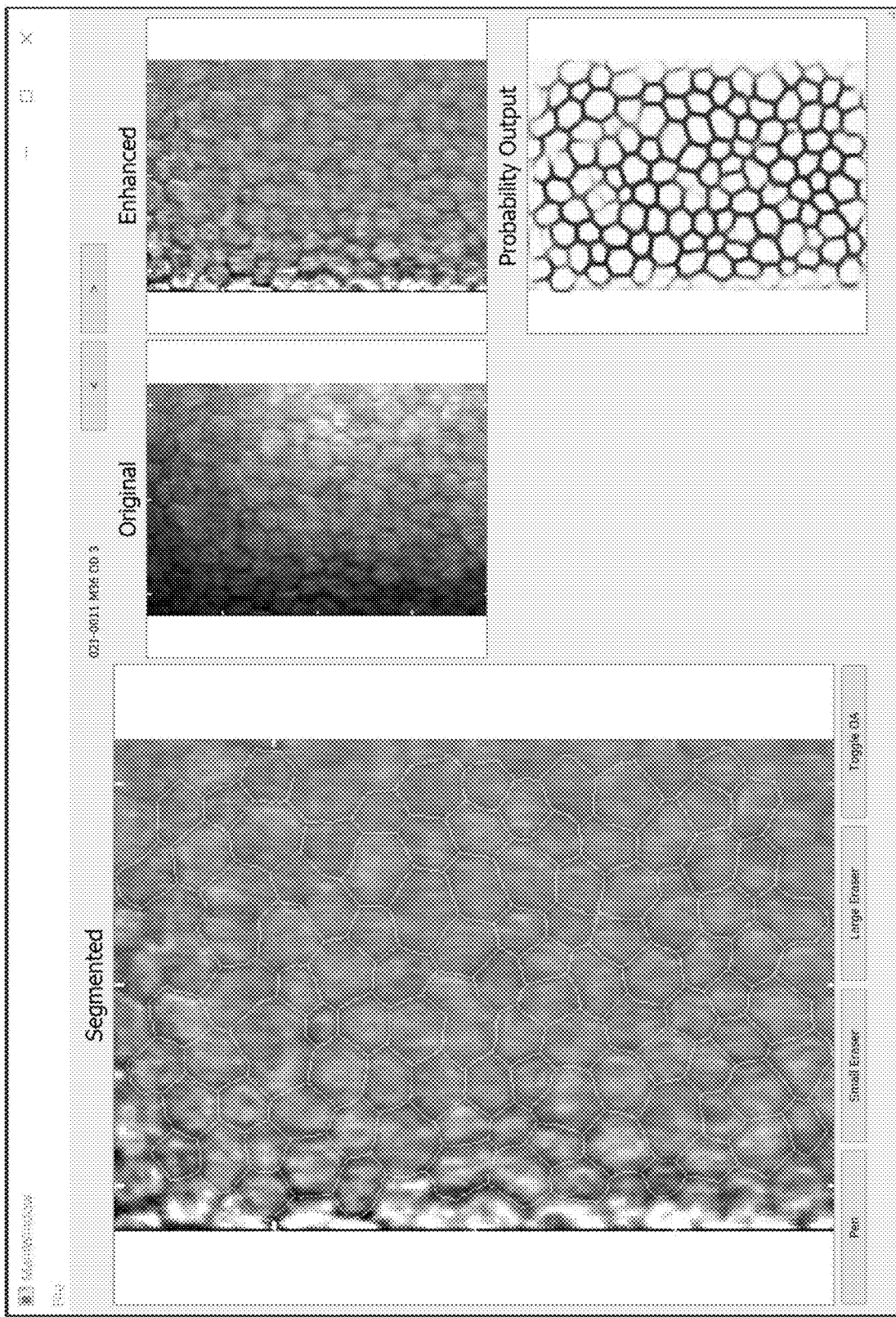
FIG. 23 illustrates an example screenshot of semi-automated segmentation graphic user interface (GUI) software, in connection with various aspects discussed herein.

Referring to FIG. 23, illustrated is an example screenshot of semi-automated segmentation graphic user interface (GUI) software, in connection with various aspects discussed herein. In the large viewing window, the GUI displays the enhanced EC image with the automatic segmentations overlay. On the side, the user can see the original raw EC image, the flattened, enhanced EC image, and the probability output to cross reference information and to aid during the manual editing process. Below the large viewing window, the user has the option to select a pen for adding cell borders, and two sizes for erasing cell borders. There is also a button to toggle between the automatic border segmentation and the highlighting of cells that may require a second review.

Figure 24:
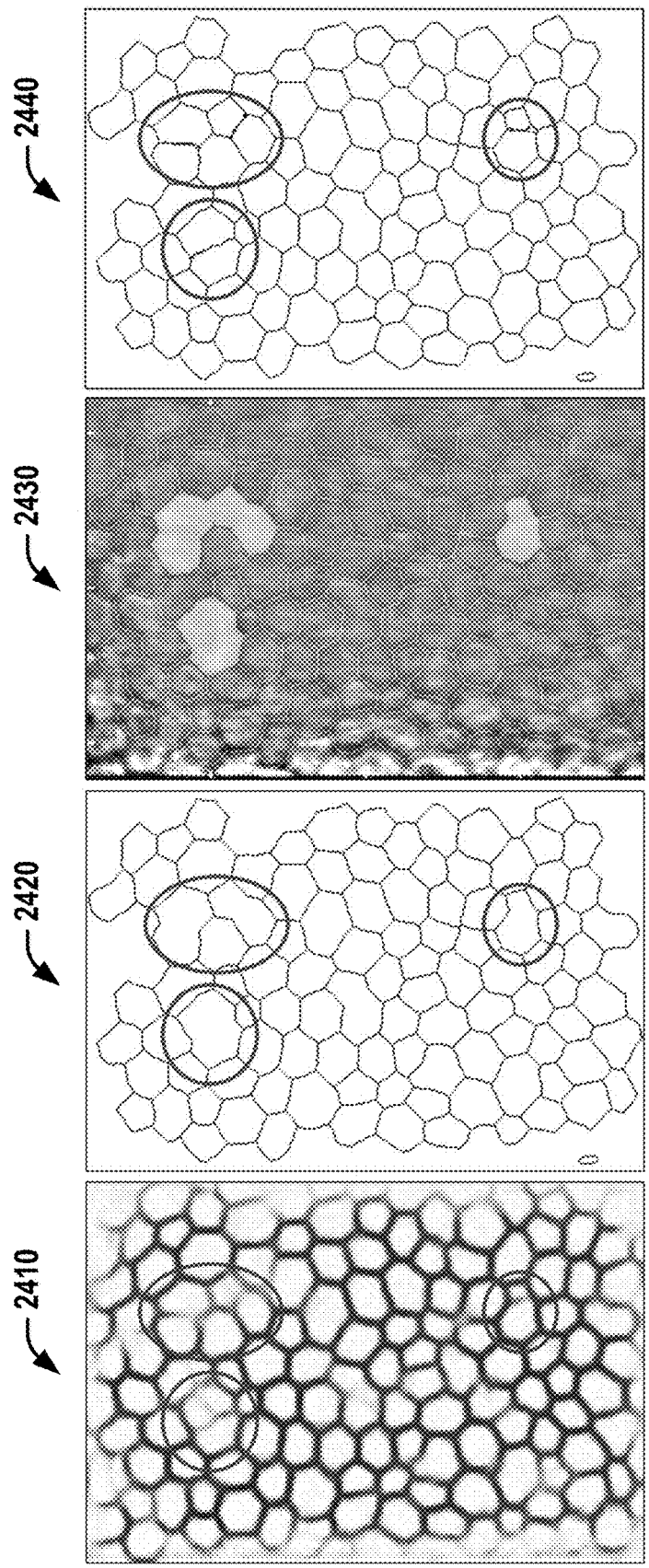
FIG. 24 illustrates example images showing cells with outlier areas or cells that were under-segmented and/or had faint or incomplete borders noticeable in the corresponding cell's area of the probability output, in connection with various aspects discussed herein.

Referring to FIG. 24, illustrated are example images showing cells with outlier areas or cells that were under-segmented and/or had faint or incomplete borders noticeable in the corresponding cell's area of the probability output, in connection with various aspects discussed herein. Circles indicate cells that matched these two conditions. At 2410 is the U-Net probability output. At 2420 is the final automatic segmentations. At 2430 is the enhanced EC imaged with automatic segmentation overlay and erroneous cells highlighted for second review. At 2440 are manual edits applied to automatic segmentation using the pen tool in the GUI software.

Figure 25:
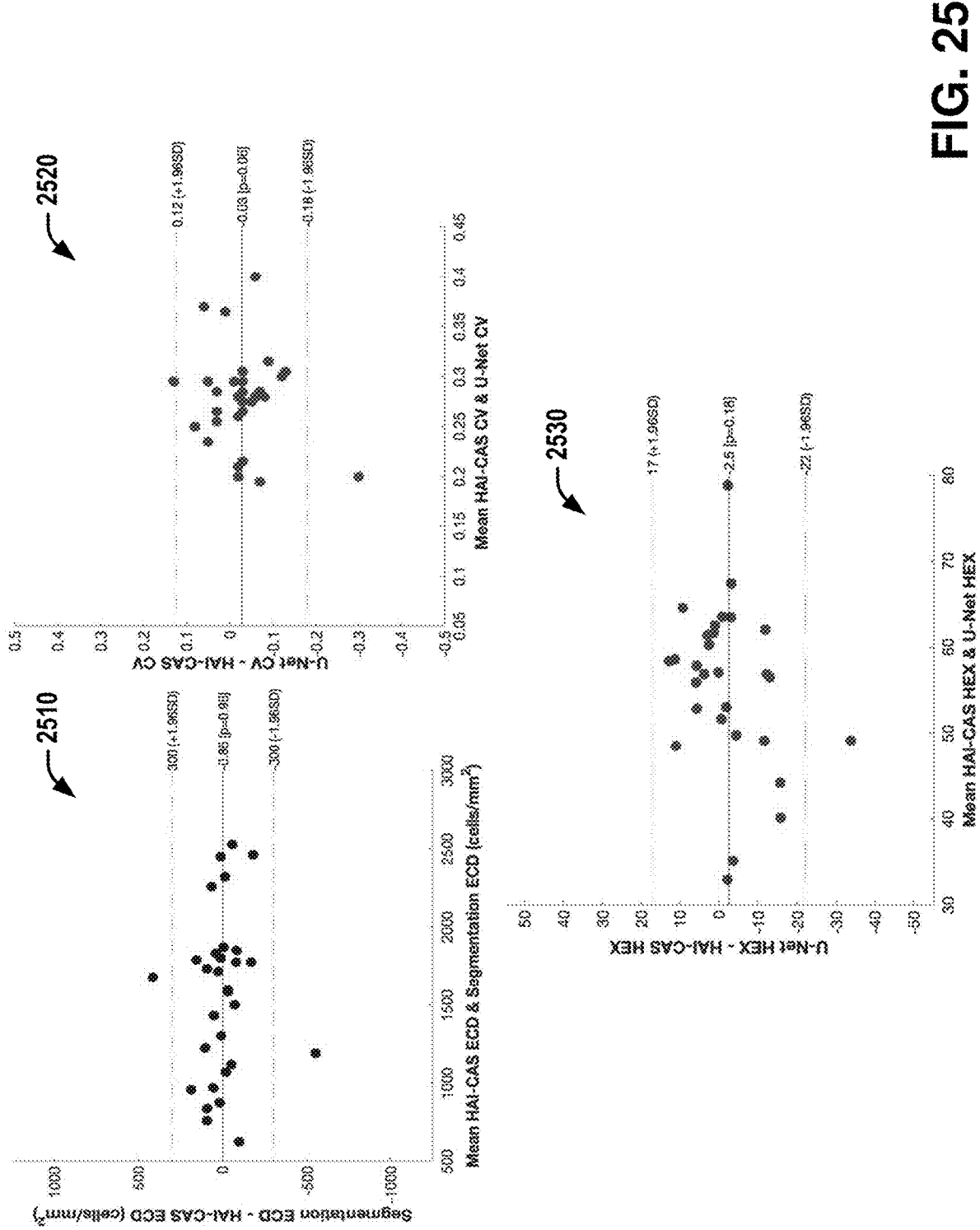
FIG. 25 illustrates Bland Altman plots for endothelial cell density (ECD), coefficient of variation (CV) of cell area, and hexagonality (HEX), in connection with various aspects discussed herein.

Referring to FIG. 25, illustrated are Bland Altman plots for ECD, CV, and HEX, in connection with various aspects discussed herein.

Figure 26:
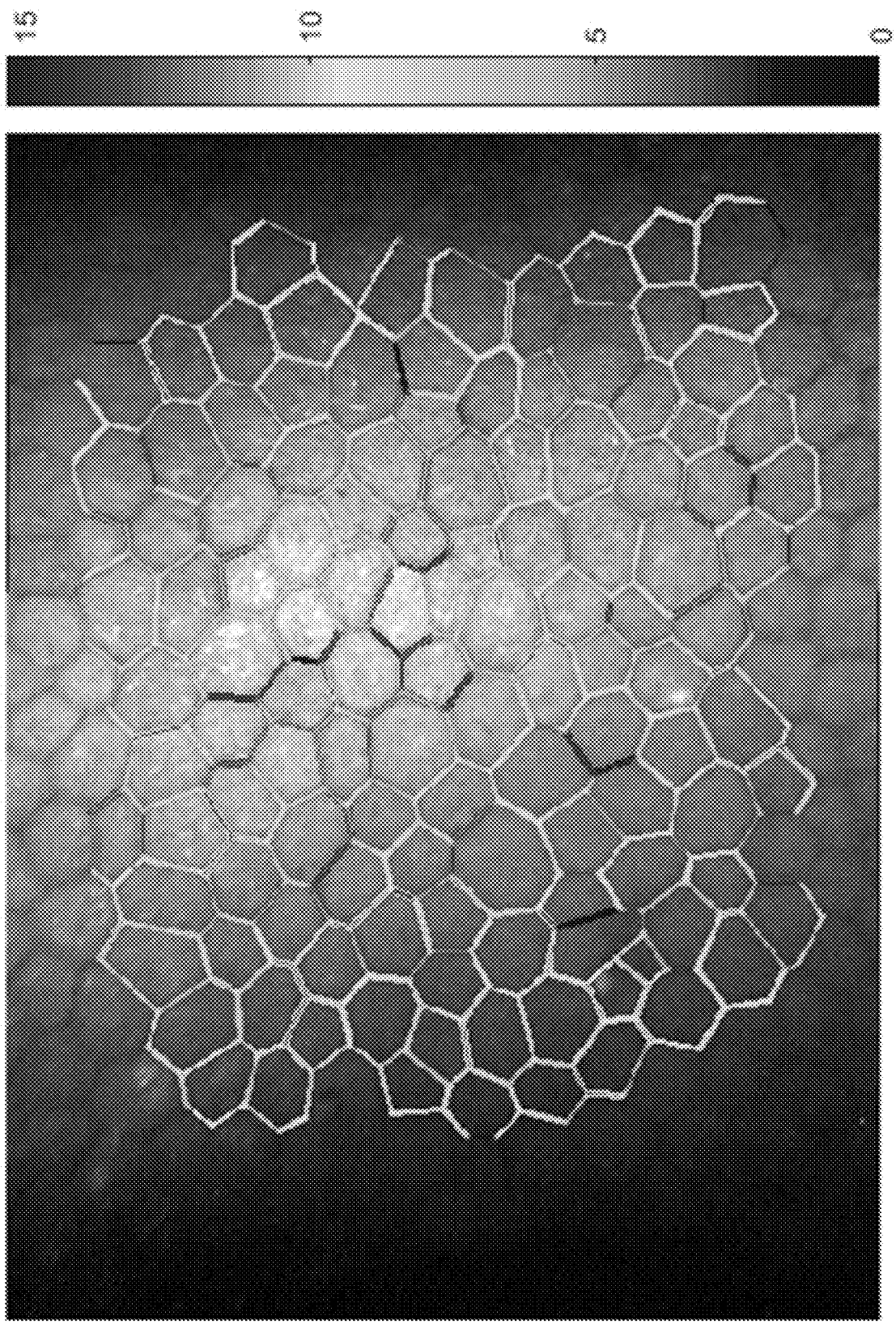
FIG. 26 illustrates a heatmap of an example EC image, showing border thickness, in connection with various aspects discussed herein.

Referring to FIG. 26, illustrated is a heatmap of an example EC image, showing border thickness, in connection with various aspects discussed herein. Border thickness was measured from EC images because it is believed that when the cornea swells, the cell borders of the endothelium will thicken.

Figure 27:
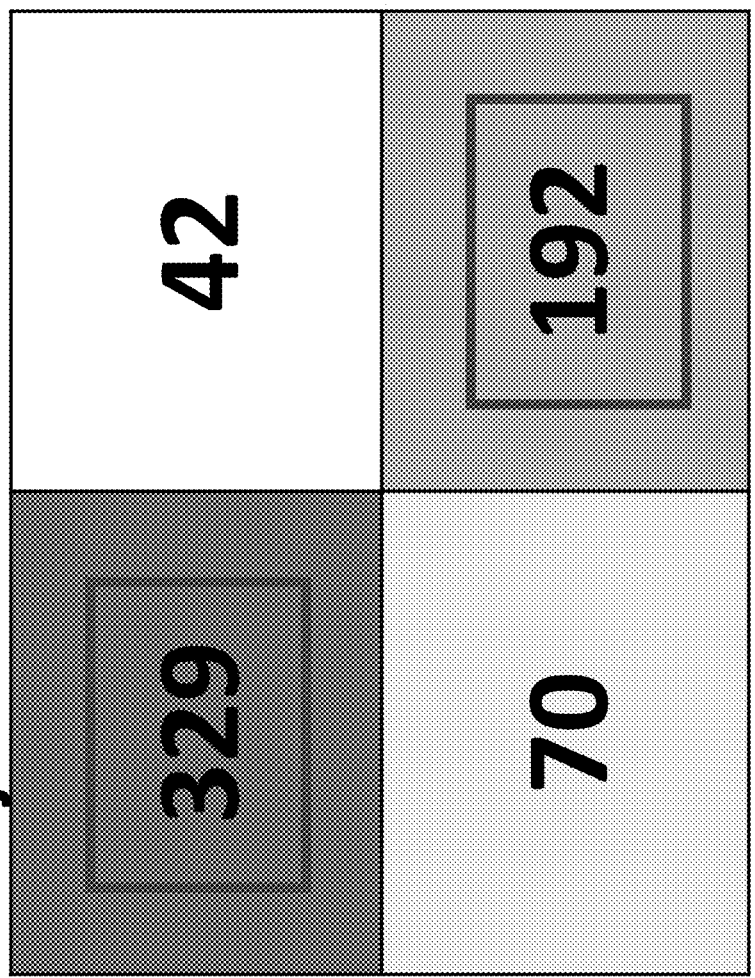
FIG. 27 illustrates a confusion matrix showing predicted and actual classification results for a machine learning classifier trained and tested on a small cohort of EC images from the Netherlands Institute of Innovative Ocular Surgery, in connection with various aspects discussed herein.

Referring to FIG. 27, illustrated is a confusion matrix showing predicted and actual classification results for a machine learning classifier of the first example use case, in connection with various aspects discussed herein. A small data cohort of 28 patients with 633 EC images was used to train a random forest machine learning classifier (with 5-fold cross validation, as discussed above) to predict keratoplasty rejection. From the confusion matrix, out of 371 EC images from rejection eyes, the model accurately classified 329 images as rejection, giving a sensitivity of 0.8868, and correctly identified 192 of the 262 control images, for a specificity of 0.7328.

Once trained, the algorithm can be deployed to analyze EC images for the risk of failure or rejection. All training can be encoded in a deployed machine learning model. Various embodiments can be deployed on a stand-alone computer or distributed over the internet from a server. Additionally, as more data becomes available, learning algorithms can be trained on more data, and new model(s) created for deployment.

Example Use Case 2: Semi-Automated Segmentation of Corneal Endothelial Images The following discussion provides example embodiments in connection with a second example use case involving automated and semi-automated segmentation of corneal endothelial images via a trained deep learning (DL) model.

Abstract

Corneal endothelial cell (EC) layer images are utilized to indirectly assess the health of the cornea post-transplantation. Cellular, morphological biomarkers of cornea health are computed from these images, but first they require manual or automatic segmentation of cells and cell borders. As manual segmentation is very time consuming, the second example use case developed a semi-automated approach. A deep neural network architecture (U-Net) was used to segment cells in specular microscopy images of the corneal endothelium, with a 0.87 Dice coefficient on a per image basis. A visual study analyzed newly identified and split/merged cells in the automatic segmentation results as compared to annotations. It was determined that 53 (3%) of the 1,867 cells in 30 test EC images benefited from an additional manual edit. Of the 30 test images, 6 had no edits, 20 had 1-3 edits, and 4 had 4-5 edits. Based on these results, any new image is likely to have 1-3 discrepancies between the manual and automatic segmentation. These segmentation differences generally occur in the dark areas or regions with unclear borders in the images, and are easily fixed with the addition or deletion of a border. Interactive software was designed in connection with the second example use case that highlighted specific borders/areas, where segmentations are suspicious, for potential editing. There are multiple criteria for suspicious cells (e.g., outlier cell areas with respect to the average cell area in a given image and under-segmented cells with visible faint or disconnected borders in the DL (e.g., U-Net) output images). This approach can allow clinicians and expert analysts to analyze images in 1-2 minutes as compared to 20 minutes now, likely with reduced inter-reader variability. This will enable efficient and precise research studies involving several hundreds of images in the prediction of corneas at risk.

1. Introduction

For the second example use case, an automatic segmentation method was developed to delineate the dark cell borders of endothelial cell (EC) images following a corneal transplant, one of the most common transplants performed with over 44,000 surgeries annually. A healthy EC layer maintains a clear cornea via an active ion-pump mechanism, which redistributes fluid from the anterior chamber through the cornea. These healthy cells are usually hexagonally shaped, with similar area, and are uniformly aligned without large gaps in-between cells. Over time however, corneal ECs start to die but are never replaced by dividing cells. Instead, surrounding ECs morph, compromising their uniform shape and size. This hinders the ion-pumps mechanism, causing fluid to build up in the cornea turning it opaque-like and deteriorating vision. Treatment options include topical steroids, but a more successful option is undergoing a keratoplasty. There are three types of keratoplasty treatment available: penetrating keratoplasty (PK), Descemet stripping automated endothelial keratoplasty (DSAEK), and Descemet membrane endothelial keratoplasty (DMEK). Each transplant varies based on how much of the donor's cornea is extracted and implanted into the recipient's eye.

Following a transplant, clinicians perform regular follow-ups, analyzing the cornea and the EC layer ensuring clarity and overall health. Clinicians commonly use quantitative biomarkers, endothelial cell density (ECD), coefficient of variation (CV), and percent hexagonality (HEX), of the EC layer to evaluate cornea health post-transplantation. Briefly, ECD is the number of cells per total sample area of cells in the image, CV is the standard deviation of cell area divided by the mean cell area within the image, and HEX is the percentage of cells that have six sides. However, in order to calculate these morphometrics, the cells and their borders need to be identified in the EC layer. This is made difficult due to the various cell sizes and shapes, varying illumination, unclear cell and border distinction, and sometimes poor image quality. The delineation of cell borders can be done manually, or automatically. Manual segmentation is a laborious process, and there is increased risk of inter-reader variability when it comes to making decisions about classifying an uncertain region. Automatic segmentation, such as watershed algorithms, genetic algorithms, and region-contour and mosaic recognition algorithms, while much quicker and more consistent, may still make errors when trying to segment the uncertain regions. Deep learning (e.g., U-Net neural network, etc.) has shown promising results for segmenting corneal ECs. These studies have been trained and conducted on various datasets such as non-diseased eyes, glaucomatous eyes, or with cell centroid-marked ground truths.

For the second example use case, a semi-automatic deep learning approach was developed to segment the cell borders of EC images post-DSAEK. This approach starts with applying a U-Net learning system convolutional neural network to train and segment 130 specular-microscope, clinical quality, post-transplant EC images acquired in the Cornea Preservation Time Study (CPTS). However, as mentioned previously, automatic segmentation may make a couple of errors, thus an automatic segmentation guided correction graphical user interface (GUI) software was also created for users to directly address segmentation errors by either adding or erasing cell borders. The GUI software also aids users by highlighting cells with borders that are potentially incorrect. These manual edits would likely involve 1 to 2 additional minutes after the automatic segmentation step.

2. Image Processing and Analysis

The deep learning architecture U-Net is employed to classify each pixel in the EC images into one of two classes: cell border or other. Probability outputs from the network show areas of high and low classification confidence. A post-processing pipeline was applied to the segmentation probability outputs following the classification step to binarize, thin, and prune the cell borders until each border encompasses a full cell. Alongside conducting a quantitative analysis to evaluate the deep learning segmentation performance, a visual analysis was carried out. An ophthalmologist and expert reader analyst evaluated each test image cell-by-cell difference between the ground truth and segmentation results to determine which method (automated or manual) accurately segments the cell borders. The results of the visual analysis indicate that a couple manual edits can improve the cell border segmentation on most images.

2.1 U-Net Deep Learning Segmentation

Figure 28:
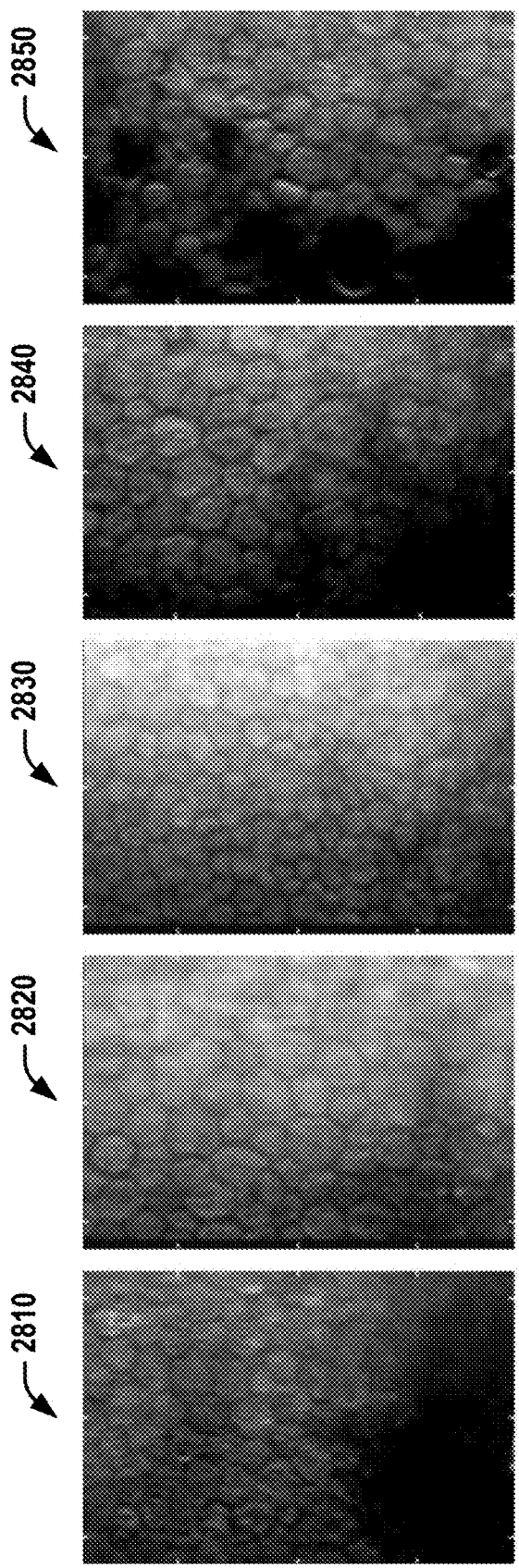
FIG. 28 illustrates five examples of clinical quality EC images taken at various time points following DSAEKs with this illumination gradient, in connection with various aspects discussed herein.

The U-Net deep learning segmentation begins with pre-processing the EC images to remove the illumination gradient that exists across the images from left to right. Referring to FIG. 28, illustrated are five examples (2810-2850) of clinical quality EC images taken at various time points following DSAEKs with this illumination gradient, in connection with various aspects discussed herein. To remove this gradual change from dark to light intensity, a Gaussian filter was applied with standard deviation s=21 and kernel footprint (65×65 pixels), producing a background image. The original EC image was divided by this background image, and then the 99th percentile of the image's intensity was set to 255 before normalizing the rest of the image's intensity within the range (0, 255).

After pre-processing the EC images, the U-Net neural network architecture shown in FIG. 15 was used, which has shown promising results with regards to image segmentation. U-Net has many advantageous features such as its decoding (downsampling), encoding (upsampling), and skip connections, allowing the network to recover full spatial resolution in its decoding layers. The architecture contained 16 layers and has a receptive field of size (93, 93). U-Net produces probability output images with pixel values between 0 and 1. Values closer to 0 indicate strong confidence of a cell's border, and values closer to 1 indicate strong confidence of a cell or other surrounding.

Following U-Net, the probability output images underwent a post-processing pipeline to binarize and clean up the cell borders until the result was a binary image with single pixel-width black borders that fully enclosed white cells. This pipeline started with first upscaling the probability outputs from values (0 to 1) to create (0 to 255) grayscale images. Then the images were inverted before adaptive Otsu thresholding to binarize the probabilities. The window of the adaptive threshold was approximately ⅛th the size of the image. This binary image was then inverted so the cell borders were white, and the cells/surrounding pixels were black. The image then underwent five morphological operations to create thin borders between cells and to clean the binarized result. First, a morphological closing operation was performed with a structuring element consisting of a disk with radius 4 to close cell borders with gaps from the binarization process. Second, the result was processed with a thinning operation. Thinning results in 1-pixel wide cell borders, thereby matching the width in the ground truth labels. Third, a flood-fill operation was applied, delineating all cells and borders white, and the surrounding area black. This process left small erroneous cell border segmentations outside the primary segmentation regions. Fourth, a morphological area opening operation was performed to identify and remove 4-connected pixels or any connected components less than 50 pixels. This image was multiplied by the inverse of the image produced after the second manipulation. Finally, the fifth morphological operation, a pruning operation, was applied to the product image to remove spurs and stray lines prior to inverting the image once more. The result was a binary image with single-pixel width black borders that were closed and fully encapsulated white cells, with white surrounding area.

2.2 Visual Analysis

A quantitative approach was applied to the 30 held-out test images of the dataset, calculating the Dice coefficient and Jaccard index. However, this may not tell the full story of the segmentation process, because sometimes the automated method would segment cells outside the region of the manually segmented region. There was no way to evaluate the accuracy of the newly identified cells outside the ground truth region. Furthermore, there were a few over or under-segmented cells within the ground truth region where it was difficult to determine which method accurately segmented the cell border. This was more common when cell borders were obstructed by bright and dark spots in the imaging technology. Thus, a visual analysis study was performed where an ophthalmologist and expert EC reader analyst evaluated each image on a cell-by-cell basis answering the following two questions: (1) When automated and manual cell detections differ (e.g., automated method identifies two cells and manual identifies one cell or vice versa), which method (manual, automatic, or an equivocal case) correctly segmented the cell (The number of discrepancies per image when answering this question was recorded as well) and (2) For each newly identified cell, was it automatically segmented accurately, inaccurately, or is it an equivocal case.

2.3 Semi-Automated Segmentation GUI

Software was developed to enable rapid manual editing following the automatic U-Net deep learning segmentation discussed above. Since U-Net may make a few mistakes when segmenting cell borders in challenging images, guided correction software was created whereby an operator can quickly identify suspicious cells for correction. A graphical user interfaced (GUI) was created in the Python programming language version 3.7. The software displays four images so the user can cross reference different information from each image in order to make an informed decision regarding where to add or erase a new or erroneous cell border, respectively. The four corresponding images include the original raw EC image, the enhanced, pre-processed EC image, the probability maps from the U-Net segmentation, and the final segmentation border image after post-processing overlaid on the enhanced, pre-processed EC image. The GUI has a pen and eraser tool for editing the segmentation image.

Two conditions were implemented to identify suspicious cells for editing in each image. Suspicious cells were defined as over-segmented (when one true cell has been split into two or more cells) or under-segmented (when two or more cells have been merged into one cell). The automatic segmentation produced more under-segmented cells than over-segmented.

The algorithms for identifying under-segmented cells follow. First, under-segmented cells can be identified by excessively large areas in comparison to the rest of the cells in the image. Thus, a first way to identify suspicious cells calculated the area of each cell in an image and identified outlier cell areas based on those cells having an area exceeding an associated threshold (e.g., identifying outliers as having area greater than 3 standard deviations higher than the mean cell area in the image). Second, under-segmented cells can be identified by altering the local threshold value within a cell prior to binarizing the U-Net probability output. If the change in local threshold value leads to two or more cells instead of a single cell, the segmented cell is highlighted for a second review. The intuition behind this second condition is that there are borders in the U-Net probability outputs that may not be as dark as nearby cell borders, or they are disconnected. When the adaptive threshold is determined for a pixel's neighborhood, the fainter borders' intensities fall above the threshold value. Thus, during binarization these faint borders are classified as cells instead of borders and the resulting cell is under-segmented.

To identify over-segmented cells, cells were highlighted that have much smaller areas than the average cell area. Similar to the under-segmentation approach, suspicious cells were identified that have excessively small areas in comparison to the rest of the cells in the image. The area of each cell in the image was calculated, and cells with areas that are lower than an associated threshold (e.g., cells with area greater than 3 standard deviation lower than the mean cell area, etc.) in the image were identified as potentially over-segmented.

3. Experimental Methods 3.1 Labeled Dataset

The EC images used in this study were retrospectively obtained from the Cornea Image Analysis Reading Center (CIARC) along with their corresponding corner analysis performed in HAI CAS/EB Cell Analysis System software (HAI Laboratories, Lexington, MA). A subset of 130 images were randomly selected from the CPTS clinical research study, which acquired EC images from 1330 eyes taken at various time points between 6- to 48-months post-DSAEK. All images used were size (446×304) pixel with pixel area of 0.65 $\mu m^2$ and were taken with Konan specular microscopes (Konan Medical, Irvine, California). Each image contained between 8-130 cells that were manually identified and their borders were segmented. The EC densities of these images ranged from 600 to 2450 cells/$mm^2$. All images were deidentified and handled in a method approved by the University Hospitals Cleveland Medical Center Institutional Review Board.

All images were manually analyzed using the standard operating procedures of the Reading Center. Trained readers from the Reading Center utilized the HAI corners method to manually segment the cell borders of the raw EC images. The readers mark cell corners with the HAI CAS/EB software (HAI Laboratories, Lexington, Massachusetts) and then the software generated cell borders connecting the corners. FIG. 17, discussed above, shows the manual segmentation applied to an example EC image. Note in the second image that occasionally the green cell border segmentations overlap. To remedy this, the segmentations were dilated and thinned to created single pixel width borders.

3.2 Classifier Training and Testing

For training the U-Net architecture, 100 images from the 130 EC image dataset was used for training and the remaining 30 images for testing. A 10-fold cross validation to training approach was used, where 90 images of the training dataset were used for training, and 10 images were used for validation. Training stopped when validation loss performance on the validation set did not improve.

Prior to the training process, the EC images were padded on all sides in a symmetric fashion to ensure the convolutions are valid at the edges. U-Net was trained for a maximum of 200 epochs, using weighted binary cross entropy as its loss function. Class imbalance could be accounted for by weighting the loss function by the inverse of the observed class proportions. For example, in the second example use case, cell borders occurred at a low frequency across all EC images (about 5% of the pixels) whereas cells or other accounted from about 95% of the pixels. Therefore, cell border pixels will have a larger weight in the computation of the lass function. The network was optimized using the Adam optimizer with an initial learning rate of 1.0e-4. Finally, data augmentation was utilized to ensure good generalization performance by the network.

Briefly, the augmentations used were in the range of 5% translations in height and width across the image, 5% zoom, 3 degree shear, and random horizontal flips. The model with the lowest validation-loss value during the training phase was applied to the 30 image held-out test set.

Software for image pre-processing and binarizing the network predictions were implemented using MATLAB R2018a. U-Net was implemented using the Keras API (with Tensorflow as backend), the Python programming language. Neural network training was performed using two NVIDIA Tesla P100 graphics processing unit cards with 11 GB RAM on each card.

4. Results

FIG. 22, discussed above, shows results of the automatic segmentation algorithm on three held-out test EC images. In the overlay images, there are red cells outside the ground truth cell region in green, which is indicative of the algorithm's ability to segment newly identified cells. Additionally, there is the occasional cell or two where there is a discrepancy between the manual and automatic segmentation in white circles. These white circles correspond to the red circles seen on the probability output images where a faint or disconnected border is visible within the cell's interior region. These cells and areas are example cases of challenging or uncertain regions that the software can highlight for a manual follow-up correction.

The quantitative results from the U-Net automatic segmentation (prior to manual editing) and visual analysis study were as follows. The manual segmentations found 1876 cells in the 30 test images. When quantitatively comparing these cells to the corresponding cells of the automated segmentation, the average cell Dice coefficient across all 30 test images was 0.87. The automated segmentations found an additional 507 cells. The expert analyst and ophthalmologist declared 293 (57%) of the new cells accurate, 93 (18%) cells inaccurate, and 123 (24%) cells equivocal. There were 53 (3%) cell discrepancies between the manual and automated segmentations of the 1876 manually graded cells. The manual segmentation correctly segmented 44 (83%) of the discrepancies, while the automatic segmentation method correctly segmented 1 (2%) of them leaving 8 (15%) of the discrepancies as incorrectly segmented by both methods.

Manual editing can be accomplished via the semi-automated segmentation GUI developed and shown in FIG. 23, discussed above. The GUI loads four images for a single eye: the original raw EC image, the pre-processed image, the probability output image, and the overlay of the automatic segmentation results on the pre-processed image. It was determined that the main viewing window should display the enhanced EC image instead of the raw image because the enhanced image can show cells more clearly in the darker regions of the original image. In the top left corner of the enhanced and the original images in FIG. 23, the cells are clearer and their borders are more apparent in the enhanced EC image.

As mentioned previously, there were less than 3% of cell discrepancies, or suspicious cells as described earlier, between the manual and automatic segmentations. Some of these discrepancies were due to faint borders in the probability output images that had higher intensity levels compared to neighboring cell borders, and were ultimately classified as not a border due to the lower local threshold value in particular region. Other times, these potential cell borders were disconnected and did not fully enclose a cell in the probability output. Then, during the post-processing pipeline, even if the disconnected border was classified as a border (when the image was binarized), it would be removed by the area opening or the pruning morphological operation, thus merging two or more cells into one big under-segmented cell. Other times, these discrepancies occurred because U-Net was trying to segment cells in a poor quality region of an image segmented a bigger "cell" that may not have been present. Less common, but still prevalent, were over-segmented cell discrepancies, when one cell was split into two or more cells. Usually, this was due to a dark curve segment inside the cell that could have been mistaken for a cell border. Since this occurred less frequently, the under-segmented cells were primarily addressed within the GUI.

Thus, two methods were implemented to filter for these under-segmentation cases and highlight such cells for a second review. Briefly again, the first condition addressed cells with areas that were greater than 3 standard deviations away from mean cell area within a given image. The second condition addressed cells where, if the local threshold was altered within the cell's interior, more cell borders became apparent, splitting the once large cell into two or more real cells. These two methods were able to highlight a total of 167 cells across the 30 held-out test images. FIG. 24, discussed above, shows an example of an EC image with cells that were highlighted for a second revision. Within the red circles of the probability output in FIG. 24, there are multiple disconnected border pixels that were eventually classified as cell pixels as shown in the final automatic segmentation image 2420. However, the method of altering the local threshold within a single cell's interior resulted in the identification of these borders, thus they have been highlighted in the third image 2430. Using the pen tool in the GUI software, borders were manually draw in and can be seen in the red circles of the fourth image 2440. Such edits would only take an extra 1 to 2 minutes after loading the images into the GUI software.

5. Discussion

U-Net proved to be a sufficient learning system with regards to automatic segmentation of cell borders in clinical quality EC images post-keratoplasty. Quantitatively, the automatic segmentation algorithm, including pre-processing, the U-Net neural network, and post-processing pipeline was able to produce EC segmentations with Dice coefficient of 0.87. However, there were over 500 newly identified cells in the held-out test set that could not be quantitatively analyzed because there weren't ground truth cells to compare against. Of the newly identified cells, only 9% would require manual editing. Furthermore, there were a couple cells (less than 3%) within the ground truth region that were either over- or under-segmented by the algorithm. Thus, after performing the visual analysis study, it was evident a couple manual edits were often involved for the images to be an accurate representation of the cell borders within the images.

The second example use case developed a semi-automated segmentation GUI software allowing users to compare information from the original EC image, enhanced EC image, probability output, and segmentation border overlay on the enhanced EC image to make an informed decision about where to manually edit the final automatic segmentation. The GUI software highlights cells based on their area with respect to the average cell area within the image. It also identifies cells that have been under-segmented, where based on the probability output from U-Net, border pixels may not have been classified because the local threshold value in the cell region was too low. Manual editing following automatic segmentation could be done in 3-5 minutes or less, which is much less in comparison to the 15-30 minutes now required for a full EC image manual segmentation.

In summary, automated segmentation of cell borders using dep learning is successful even in challenging post-transplant EC images. While EC automatic segmentation accuracy is very good, a couple small manual edits to each image could improve the accuracy even more. An interactive semi-automated segmentation GUI software allows informative viewing and easy editing of these EC images, assisting in potential future work of collecting accurate clinical morphometric calculations when helping physicians assess the healthiness of corneal transplants.

Additional Embodiments

In various example embodiments, method(s) discussed herein can be implemented as computer executable instructions. Thus, in various embodiments, a computer-readable storage device can store computer executable instructions that, when executed by a machine (e.g., computer, processor), cause the machine to perform methods or operations described or claimed herein including operation(s) described in connection with methods 100, 200, 300, 400, or any other methods or operations described herein. While executable instructions associated with the listed methods are described as being stored on a computer-readable storage device, it is to be appreciated that executable instructions associated with other example methods or operations described or claimed herein can also be stored on a computer-readable storage device. In different embodiments, the example methods or operations described herein can be triggered in different ways. In one embodiment, a method or operation can be triggered manually by a user. In another example, a method or operation can be triggered automatically.

Embodiments discussed herein relate to training and/or employing deep learning model(s) to automatically and/or semi-automatically segment endothelial cells based at least in part on features and/or mappings that are not perceivable by the human eye, and involve computation that cannot be practically performed in the human mind. As one example, machine learning and/or deep learning classifiers as described herein cannot be implemented in the human mind or with pencil and paper. Embodiments thus perform actions, steps, processes, or other actions that are not practically performed in the human mind, at least because they require a processor or circuitry to access digitized images stored in a computer memory and to extract or compute features that are based on the digitized images and not on properties of tissue or the images that are perceivable by the human eye. Embodiments described herein can use a combined order of specific rules, elements, operations, or components that render information into a specific format that can then be used and applied to create desired results more accurately, more consistently, and with greater reliability than existing approaches, thereby producing the technical effect of improving the performance of the machine, computer, or system with which embodiments are implemented.

Figure 29:
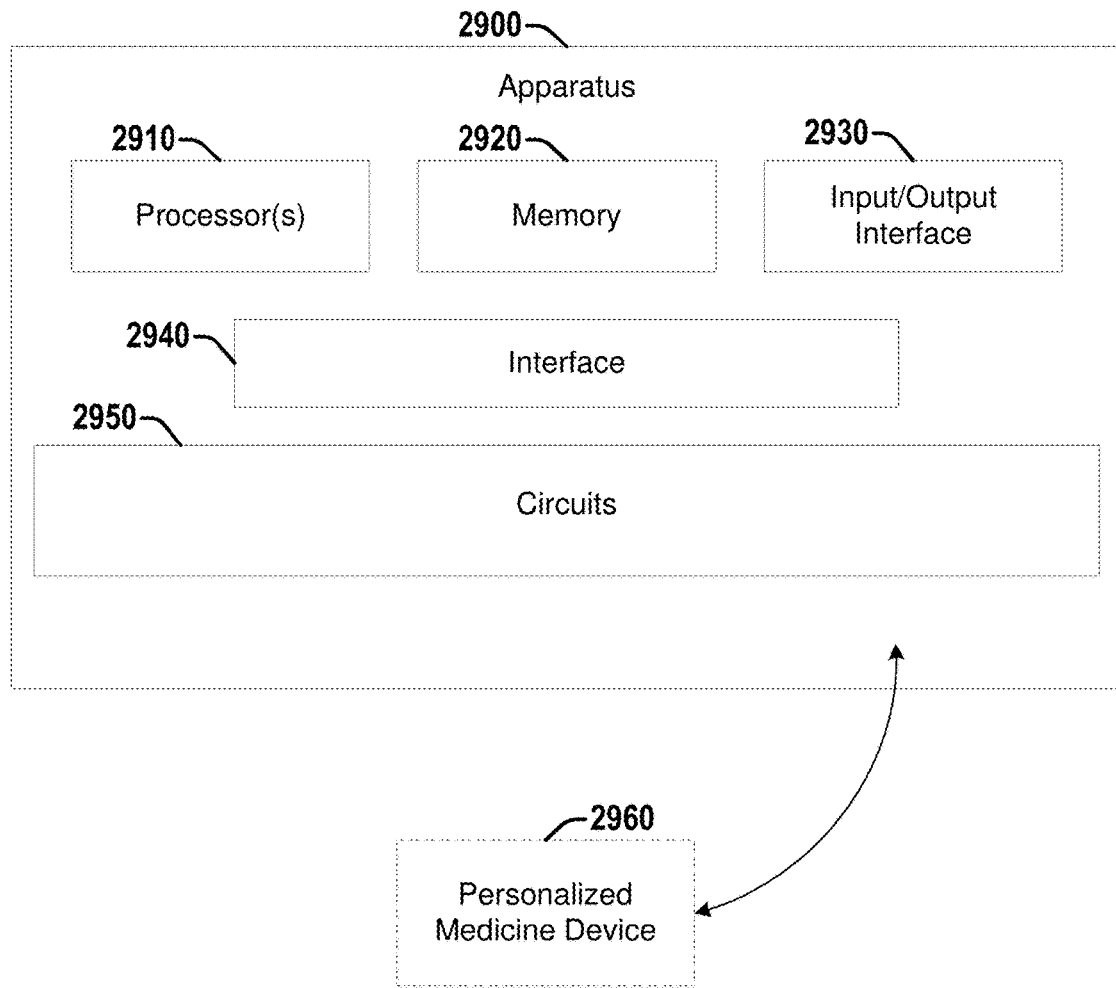
FIG. 29 illustrates a diagram of an example apparatus that can facilitate training and/or employing deep learning model(s) to automatically and/or semi-automatically segment endothelial cells, according to various embodiments discussed herein.

Referring to FIG. 29, illustrated is a diagram of an example apparatus 2900 that can facilitate training and/or employing deep learning model(s) to automatically and/or semi-automatically segment endothelial cells, according to various embodiments discussed herein. Apparatus 2800 can be configured to perform various techniques discussed herein, for example, various operations discussed in connection with sets of operations 100, 200, 300, and/or 400. Apparatus 2900 can comprise one or more processors 2910 and memory 2920. Processor(s) 2910 can, in various embodiments, comprise circuitry such as, but not limited to, one or more single-core or multi-core processors. Processor(s) 2910 can include any combination of general-purpose processors and dedicated processors (e.g., graphics processors, application processors, etc.). The processor(s) can be coupled with and/or can comprise memory (e.g., of memory 2920) or storage and can be configured to execute instructions stored in the memory 2920 or storage to enable various apparatus, applications, or operating systems to perform operations and/or methods discussed herein.

Memory 2920 can be configured to store one or more digitized microscopic images (e.g., obtained via specular or confocal microscopy, etc.) of corneal endothelial cells (e.g., for training and/or segmenting). Each of the image(s) can comprise a plurality of pixels or voxels, each pixel or voxel having an associated intensity. Memory 2920 can be further configured to store additional data involved in performing operations discussed herein, such as for determining a prognosis following keratoplasty (e.g., no adverse events vs. failure, no adverse events vs. non-rejection failure vs. rejection, etc.) from an optical microscopic image and/or training a ML or DL model to generate a prognosis for keratoplasty from an optical microscopic image, as discussed in greater detail herein.

Apparatus 2900 can also comprise an input/output (I/O) interface 2930 (e.g., associated with one or more I/O devices), a set of circuits 2950, and an interface 2940 that connects the processor(s) 2910, the memory 2920, the I/O interface 2930, and the set of circuits 2950. I/O interface 2930 can be configured to transfer data between memory 2920, processor 2910, circuits 2950, and external devices, for example, a medical imaging device (e.g., specular or confocal microscope, etc.), and/or one or more remote devices for receiving inputs and/or providing outputs to a clinician, patient, etc., such as optional personalized medicine device 2960.

The processor(s) 2910 and/or one or more circuits of the set of circuits 2950 can perform one or more acts associated with a method or set of operations discussed herein, such as set of operations 100, 200, 300, and/or 400. In various embodiments, different acts (e.g., different operations of a set of operations) can be performed by the same or different processor(s) 2910 and/or one or more circuits of the set of circuits 2950.

Apparatus 2900 can optionally further comprise personalized medicine device 2960. Apparatus 2900 can be configured to provide the segmented endothelial cells for the patient, and/or other data (e.g., keratoplasty prognosis, suggested interventions, etc.) to personalized medicine device 2960. Personalized medicine device 2960 may be, for example, a computer assisted diagnosis (CADx) system or other type of personalized medicine device that can be used to facilitate monitoring and/or treatment of an associated medical condition. In some embodiments, processor(s) 2910 and/or one or more circuits of the set of circuits 2950 can be further configured to control personalized medicine device 2960 to display the segmented endothelial cells for the patient or other data on a computer monitor, a smartphone display, a tablet display, or other displays.

Examples herein can include subject matter such as an apparatus, a microscope (e.g., specular, confocal, etc.), a personalized medicine system, a CADx system, a processor, a system, circuitry, a method, means for performing acts, steps, or blocks of the method, at least one machine-readable medium including executable instructions that, when performed by a machine (e.g., a processor with memory, an application-specific integrated circuit (ASIC), a field programmable gate array (FPGA), or the like) cause the machine to perform acts of the method or of an apparatus or system for segmenting endothelial cells and/or generating a prognosis for keratoplasty, according to embodiments and examples described.

Example 1 is a non-transitory computer-readable medium storing computer-executable instructions that, when executed, cause a processor to perform operations, comprising: accessing an optical microscopy image comprising a set of corneal endothelial cells of a patient of a keratoplasty; pre-processing the optical microscopy image to generate a pre-processed optical microscopy image via correcting for at least one of shading or illumination artifacts in the optical microscopy image; segmenting, based at least in part on a trained deep learning (DL) model, a plurality of corneal endothelial cells of the set of corneal endothelial cells in the pre-processed optical microscopy image; and displaying, via a graphical user interface (GUI), at least the segmented plurality of corneal endothelial cells.

Example 2 comprises the subject matter of any variation of any of example(s) 1, wherein the operations further comprise analyzing the segmented plurality of corneal endothelial cells to determine whether one or more cells of the segmented plurality of corneal endothelial cells are potentially under-segmented or potentially over-segmented.

Example 3 comprises the subject matter of any variation of any of example(s) 2, wherein one or more cells of the segmented plurality of corneal endothelial cells are potentially under-segmented or potentially over-segmented, and wherein the operations further comprise identifying, on the GUI, the one or more cells of the segmented plurality of corneal endothelial cells that are potentially under-segmented or potentially over-segmented.

Example 4 comprises the subject matter of any variation of any of example(s) 3, wherein the operations further comprise modifying, based on a user input, a segmentation of at least one of the one or more cells of the segmented plurality of corneal endothelial cells that are potentially under-segmented or potentially over-segmented.

Example 5 comprises the subject matter of any variation of any of example(s) 3-4, wherein the operations further comprise determining that a first cell of the one or more cells is potentially under-segmented based on the first cell having an area greater than a first threshold.

Example 6 comprises the subject matter of any variation of any of example(s) 5, wherein the first threshold is three standard deviations greater than a mean cell area of the segmented plurality of corneal endothelial cells.

Example 7 comprises the subject matter of any variation of any of example(s) 3-6, wherein the optical microscopy image comprises a plurality of pixels, wherein segmenting the plurality of corneal endothelial cells is based at least in part on a binarization threshold for identifying whether each pixel of the plurality of pixels corresponds to a cell interior or a cell boundary, and wherein the operations further comprise determining that a first cell of the one or more cells is potentially under-segmented based on the first cell corresponding to two or more cells when the segmentation threshold is changed.

Example 8 comprises the subject matter of any variation of any of example(s) 3-7, wherein the operations further comprise determining that a first cell of the one or more cells is potentially over-segmented based on the first cell having an area lower than a first threshold.

Example 9 comprises the subject matter of any variation of any of example(s) 8, wherein the first threshold is three standard deviations lower than a mean cell area of the segmented plurality of corneal endothelial cells.

Example 10 comprises the subject matter of any variation of any of example(s) 1-9, wherein the DL model is a convolutional neural network (CNN).

Example 11 comprises the subject matter of any variation of any of example(s) 10, wherein the CNN has a U-Net architecture.

Example 12 comprises the subject matter of any variation of any of example(s) 1, wherein the segmenting comprises performing binarizing a probability map generated by the DL model based on one of an adaptive threshold or an Otsu threshold.

Example 13 is a non-transitory computer-readable medium storing computer-executable instructions that, when executed, cause a processor to perform operations, comprising: accessing a training set comprising a plurality of optical microscopy images, wherein each optical microscopy image of the training set comprises an associated set of corneal endothelial cells of a patient associated with that optical microscopy image, and wherein each optical microscopy image of the training set is associated with a ground truth segmentation of plurality of corneal endothelial cells of the set of corneal endothelial cells of that optical microscopy image; pre-process each optical microscopy image of the training set to correct for at least one of shading or illumination artifacts; and based at least on each pre-processed optical microscopy image and the ground truth segmentation for each optical microscopy image, training a deep learning model to segment a plurality of corneal endothelial cells of a set of corneal endothelial cells of an additional pre-processed optical microscopy image.

Example 14 comprises the subject matter of any variation of any of example(s) 13, wherein the deep learning model is a convolutional neural network (CNN).

Example 15 comprises the subject matter of any variation of any of example(s) 14, wherein the CNN has a U-Net architecture.

Example 16 is an apparatus, comprising: memory configured to store an optical microscopy image comprising a set of corneal endothelial cells of a patient of a keratoplasty; one or more processors configured to perform operations comprising: pre-processing the optical microscopy image to generate a pre-processed optical microscopy image via correcting for at least one of shading or illumination artifacts in the optical microscopy image; segmenting, based at least in part on a trained deep learning (DL) model, a plurality of corneal endothelial cells of the set of corneal endothelial cells in the pre-processed optical microscopy image; and displaying, via a graphical user interface (GUI), at least the segmented plurality of corneal endothelial cells.

Example 17 comprises the subject matter of any variation of any of example(s) 16, wherein the operations further comprise analyzing the segmented plurality of corneal endothelial cells to determine whether one or more cells of the segmented plurality of corneal endothelial cells are potentially under-segmented or potentially over-segmented.

Example 18 comprises the subject matter of any variation of any of example(s) 17, wherein one or more cells of the segmented plurality of corneal endothelial cells are potentially under-segmented or potentially over-segmented, and wherein the operations further comprise identifying, on the GUI, the one or more cells of the segmented plurality of corneal endothelial cells that are potentially under-segmented or potentially over-segmented.

Example 19 comprises the subject matter of any variation of any of example(s) 18, wherein the operations further comprise modifying, based on a user input, a segmentation of at least one of the one or more cells of the segmented plurality of corneal endothelial cells that are potentially under-segmented or potentially over-segmented.

Example 20 comprises the subject matter of any variation of any of example(s) 18-19, wherein the operations further comprise determining that a first cell of the one or more cells is potentially under-segmented based on the first cell having an area greater than a first threshold.

Example 21 comprises the subject matter of any variation of any of example(s) 20, wherein the first threshold is three standard deviations greater than a mean cell area of the segmented plurality of corneal endothelial cells.

Example 22 comprises the subject matter of any variation of any of example(s) 18-20, wherein the optical microscopy image comprises a plurality of pixels, wherein segmenting the plurality of corneal endothelial cells is based at least in part on a binarization threshold for identifying whether each pixel of the plurality of pixels corresponds to a cell interior or a cell boundary, and wherein the operations further comprise determining that a first cell of the one or more cells is potentially under-segmented based on the first cell corresponding to two or more cells when the segmentation threshold is changed.

Example 23 comprises the subject matter of any variation of any of example(s) 18-22, wherein the operations further comprise determining that a first cell of the one or more cells is potentially over-segmented based on the first cell having an area lower than a first threshold.

Example 24 comprises the subject matter of any variation of any of example(s) 23, wherein the first threshold is three standard deviations lower than a mean cell area of the segmented plurality of corneal endothelial cells.

Example 25 comprises an apparatus comprising means for executing any of the described operations of examples 1-24.

Example 26 comprises a machine readable medium that stores instructions for execution by a processor to perform any of the described operations of examples 1-24.

Example 27 comprises an apparatus comprising: a memory; and one or more processors configured to: perform any of the described operations of examples 1-24.

References to "one embodiment", "an embodiment", "one example", and "an example" indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

"Computer-readable storage device", as used herein, refers to a device that stores instructions or data. "Computer-readable storage device" does not refer to propagated signals. A computer-readable storage device may take forms, including, but not limited to, non-volatile media, and volatile media. Non-volatile media may include, for example, optical disks, magnetic disks, tapes, and other media. Volatile media may include, for example, semiconductor memories, dynamic memory, and other media. Common forms of a computer-readable storage device may include, but are not limited to, a floppy disk, a flexible disk, a hard disk, a magnetic tape, other magnetic medium, an application specific integrated circuit (ASIC), a compact disk (CD), other optical medium, a random access memory (RAM), a read only memory (ROM), a memory chip or card, a memory stick, and other media from which a computer, a processor or other electronic device can read.

"Circuit", as used herein, includes but is not limited to hardware, firmware, software in execution on a machine, or combinations of each to perform a function(s) or an action(s), or to cause a function or action from another logic, method, or system. A circuit may include a software controlled microprocessor, a discrete logic (e.g., ASIC), an analog circuit, a digital circuit, a programmed logic device, a memory device containing instructions, and other physical devices. A circuit may include one or more gates, combinations of gates, or other circuit components. Where multiple logical circuits are described, it may be possible to incorporate the multiple logical circuits into one physical circuit. Similarly, where a single logical circuit is described, it may be possible to distribute that single logical circuit between multiple physical circuits.

To the extent that the term "includes" or "including" is employed in the detailed description or the claims, it is intended to be inclusive in a manner similar to the term "comprising" as that term is interpreted when employed as a transitional word in a claim.

Throughout this specification and the claims that follow, unless the context requires otherwise, the words 'comprise' and 'include' and variations such as 'comprising' and 'including' will be understood to be terms of inclusion and not exclusion. For example, when such terms are used to refer to a stated integer or group of integers, such terms do not imply the exclusion of any other integer or group of integers.

To the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

While example systems, methods, and other embodiments have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and other embodiments described herein. Therefore, the invention is not limited to the specific details, the representative apparatus, and illustrative examples shown and described. Thus, this application is intended to embrace alterations, modifications, and variations that fall within the scope of the appended claims.

What is claimed is:

1. A non-transitory computer-readable medium storing computer-executable instructions that, when executed, cause a processor to perform operations, comprising:
   accessing an optical microscopy image comprising a set of corneal endothelial cells of a patient of a keratoplasty;
   segmenting, based at least in part on a trained deep learning (DL) model, a plurality of corneal endothelial cells of the set of corneal endothelial cells in the optical microscopy image;
   determining one or more cells of the segmented plurality of corneal endothelial cells that are potentially under-segmented or potentially over-segmented;
   determining that a first cell of the one or more cells is potentially over-segmented based on the first cell having an area lower than a first threshold, wherein the first threshold is three standard deviations lower than a mean cell area of the segmented plurality of corneal endothelial cells; and
   displaying, via a graphical user interface (GUI), at least the segmented plurality of corneal endothelial cells and the potentially under-segmented or potentially over-segmented cells, wherein the GUI is configured to highlight the one or more cells of the segmented plurality of corneal endothelial cells that are potentially under-segmented or potentially over-segmented and to allow a user to selectively modify cell borders of the highlighted one or more cells.

2. The non-transitory machine-readable medium of claim 1, wherein the operations further comprise identifying, on the GUI, the one or more cells of the segmented plurality of corneal endothelial cells that are potentially under-segmented or potentially over-segmented.

3. The non-transitory machine-readable medium of claim 2, wherein the operations further comprise not modifying, based on absence of a user input, a segmentation of at least one of the one or more cells of the segmented plurality of corneal endothelial cells that are potentially under-segmented or potentially over-segmented.

4. The non-transitory machine-readable medium of claim 2, wherein the operations further comprise determining that a second cell of the one or more cells is potentially under-segmented based on the second cell having an area greater than a second threshold.

5. The non-transitory machine-readable medium of claim 4, wherein the second threshold is three standard deviations greater than a mean cell area of the segmented plurality of corneal endothelial cells.

6. The non-transitory machine-readable medium of claim 2, wherein the optical microscopy image comprises a plurality of pixels and wherein segmenting the plurality of corneal endothelial cells is based at least in part on a binarization threshold for identifying whether each pixel of the plurality of pixels corresponds to a cell interior or a cell boundary.

7. The non-transitory computer-readable medium of claim 1, wherein the DL model is a convolutional neural network (CNN).

8. The non-transitory computer-readable medium of claim 7, wherein the CNN has a U-Net architecture.

9. The non-transitory computer-readable medium of claim 1, wherein the segmenting comprises performing binarizing a probability map generated by the DL model based on one of an adaptive threshold or an Otsu threshold.

10. The non-transitory machine-readable medium of claim 1, wherein the operations further comprise:
    calculating one or more features associated with the segmented plurality of corneal endothelial cells; and
    determining a prognosis for the keratoplasty based on the one or more features.

11. An apparatus, comprising:
    memory configured to store an optical microscopy image comprising a set of corneal endothelial cells of a patient of a keratoplasty;
    one or more processors configured to perform operations comprising:

pre-processing the optical microscopy image to generate a pre-processed optical microscopy image via correcting for at least one of shading or illumination artifacts in the optical microscopy image;

segmenting, based at least in part on a trained deep learning (DL) model, a plurality of corneal endothelial cells of the set of corneal endothelial cells in the pre-processed optical microscopy image;

displaying, via a graphical user interface (GUI), at least the segmented plurality of corneal endothelial cells, wherein the GUI is configured to highlight cells with borders that are potentially incorrect;

analyzing the segmented plurality of corneal endothelial cells to determine whether one or more cells of the segmented plurality of corneal endothelial cells are potentially under-segmented or potentially over-segmented; and determining that a first cell of the one or more cells is potentially under-segmented based on the first cell having an area greater than a first threshold; or determining that a second cell of the one or more cells is potentially over-segmented based on the second cell having an area smaller than a second threshold, wherein the second threshold is three standard deviations lower than a mean cell area of the segmented plurality of corneal endothelial cells.

12. The apparatus of claim 11, wherein the operations further comprise identifying, on the GUI, the one or more cells of the segmented plurality of corneal endothelial cells that are potentially under-segmented or potentially over-segmented.

13. The apparatus of claim 12, wherein the operations further comprise modifying, based on a user input, a segmentation of at least one of the one or more cells of the segmented plurality of corneal endothelial cells that are potentially under-segmented or potentially over-segmented.

14. The apparatus of claim 12, wherein the optical microscopy image comprises a plurality of pixels, wherein segmenting the plurality of corneal endothelial cells is based at least in part on a binarization threshold for identifying whether each pixel of the plurality of pixels corresponds to a cell interior or a cell boundary.

15. The apparatus of claim 11, wherein the first threshold is three standard deviations greater than a mean cell area of the segmented plurality of corneal endothelial cells.

16. The apparatus of claim 11, wherein the operations further comprise:

calculating one or more features associated with the segmented plurality of corneal endothelial cells; and determining a prognosis for the keratoplasty based on the one or more features.

17. The apparatus of claim 16, wherein the prognosis is determined via a trained machine learning model.

18. A method, comprising:

accessing an endothelial cell (EC) image comprising a set of corneal endothelial cells of a patient taken after a cornea transplantation;

performing one or more pre-processing operations on the EC image to generate a pre-processed EC image, wherein the one or more pre-processing operations modify at least one of shading or illumination artifacts in the EC image;

segmenting, based at least in part on a trained deep learning (DL) model, a plurality of corneal endothelial cells within the pre-processed EC image;

analyzing the segmented plurality of corneal endothelial cells to determine a first cell of the segmented plurality of corneal endothelial cells that is potentially under-segmented based on the first cell having an area greater than a first threshold; and displaying, via a graphical user interface (GUI), at least the segmented plurality of corneal endothelial cells and the first cell.

19. The method of claim 18, wherein the GUI is configured to identify one or more parts of a cell border of the first cell of the segmented plurality of corneal endothelial cells that is potentially under-segmented that are potentially incorrect.

20. The method of claim 18, wherein the GUI is configured to highlight the first cell of the segmented plurality of corneal endothelial cells that is potentially under-segmented to a user.

21. The method of claim 18, wherein the first threshold is three standard deviations greater than a mean cell area of the segmented plurality of corneal endothelial cells.

22. The method of claim 18, further comprising:

calculating one or more features associated with the segmented plurality of corneal endothelial cells; and determining a prognosis for the cornea transplantation based on the one or more features.

23. The method of claim 22, wherein the prognosis is one of a rejection, a failure, or a non-failure.

24. The method of claim 22, wherein the prognosis is one of no adverse outcome, non-rejection failure, or rejection.

* * * * *